(12) United States Patent
Lanigan

(10) Patent No.: US 12,201,808 B2
(45) Date of Patent: *Jan. 21, 2025

(54) AUTOMATED INSERTION ASSEMBLY

(71) Applicant: DEKA Products Limited Partnership, Manchester, NH (US)

(72) Inventor: Richard J. Lanigan, Concord, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,006

(22) Filed: Jun. 26, 2023

(65) Prior Publication Data

US 2023/0330324 A1 Oct. 19, 2023

Related U.S. Application Data

(63) Continuation of application No. 17/222,170, filed on Apr. 5, 2021, now Pat. No. 11,717,606, which is a
(Continued)

(51) Int. Cl.
*A61M 5/142* (2006.01)
*A61B 5/15* (2006.01)
(Continued)

(52) U.S. Cl.
CPC ........... *A61M 5/142* (2013.01); *A61B 5/1427* (2013.01); *A61B 5/150022* (2013.01); *A61B 5/150175* (2013.01); *A61B 5/150358* (2013.01); *A61B 5/150389* (2013.01); *A61B 5/150503* (2013.01); *A61B 5/15117* (2013.01); *A61B 5/15186* (2013.01); *A61M 5/158* (2013.01); *A61B 5/15107* (2013.01); *A61B 5/15119* (2013.01); *A61B 5/15121* (2013.01); *A61B 5/15123* (2013.01); *A61B 5/15125* (2013.01);
(Continued)

(58) Field of Classification Search
CPC .. A61M 5/142; A61M 5/158; A61M 5/14232; A61M 5/14244; A61M 5/148; A61M 2005/1581; A61M 2005/1583; A61M 2005/1585; A61M 2207/00; A61B 5/1427; A61B 5/150022; A61B 5/150175; A61B 5/150358; A61B 5/150389; A61B 5/150503; A61B 5/15117; A61B 5/15186; A61B 5/15107; A61B 5/15119; A61B 5/15121; A61B 5/15123; A61B 5/15125
See application file for complete search history.

(56) References Cited

U.S. PATENT DOCUMENTS 9,119,913 B2 * 9/2015 Lanigan ........... A61B 5/150503
10,137,241 B2 * 11/2018 Lanigan ........... A61B 5/15117
(Continued)

*Primary Examiner* — Theodore J Stigell
(74) *Attorney, Agent, or Firm* — McCormick, Paulding & Huber PLLC

(57) ABSTRACT

An automated insertion assembly includes a first dermal perforation assembly configured to releasably engage a first subdermal device. A first actuation assembly is configured to drive the first dermal perforation assembly into a user's skin to a first depth and drive the first subdermal device into the user's skin to a second depth. The second depth is greater than the first depth.

14 Claims, 26 Drawing Sheets

Related U.S. Application Data continuation of application No. 16/197,773, filed on Nov. 21, 2018, now Pat. No. 10,967,117, which is a continuation of application No. 14/840,610, filed on Aug. 31, 2015, now Pat. No. 10,137,241, which is a continuation of application No. 13/346,369, filed on Jan. 9, 2012, now Pat. No. 9,119,913, which is a continuation of application No. 12/029,234, filed on Feb. 11, 2008, now abandoned.

(60) Provisional application No. 60/889,007, filed on Feb. 9, 2007.

(51) Int. Cl.
*A61B 5/151* (2006.01)
*A61B 5/155* (2006.01)
*A61M 5/158* (2006.01)
*A61M 5/148* (2006.01)

(52) U.S. Cl.
CPC ..... *A61M 5/14232* (2013.01); *A61M 5/14244* (2013.01); *A61M 5/148* (2013.01); *A61M 2005/1581* (2013.01); *A61M 2005/1583* (2013.01); *A61M 2005/1585* (2013.01); *A61M 2207/00* (2013.01)

(56) References Cited

U.S. PATENT DOCUMENTS

| | | | |
|---|---|---|---|
| 10,967,117 B2* | 4/2021 | Lanigan | A61B 5/150389 |
| 11,717,606 B2* | 8/2023 | Lanigan | A61B 5/150358 |
| | | | 604/117 |

* cited by examiner

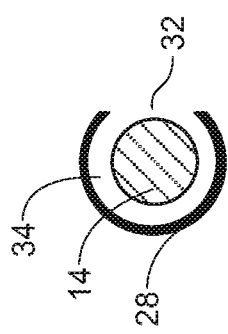
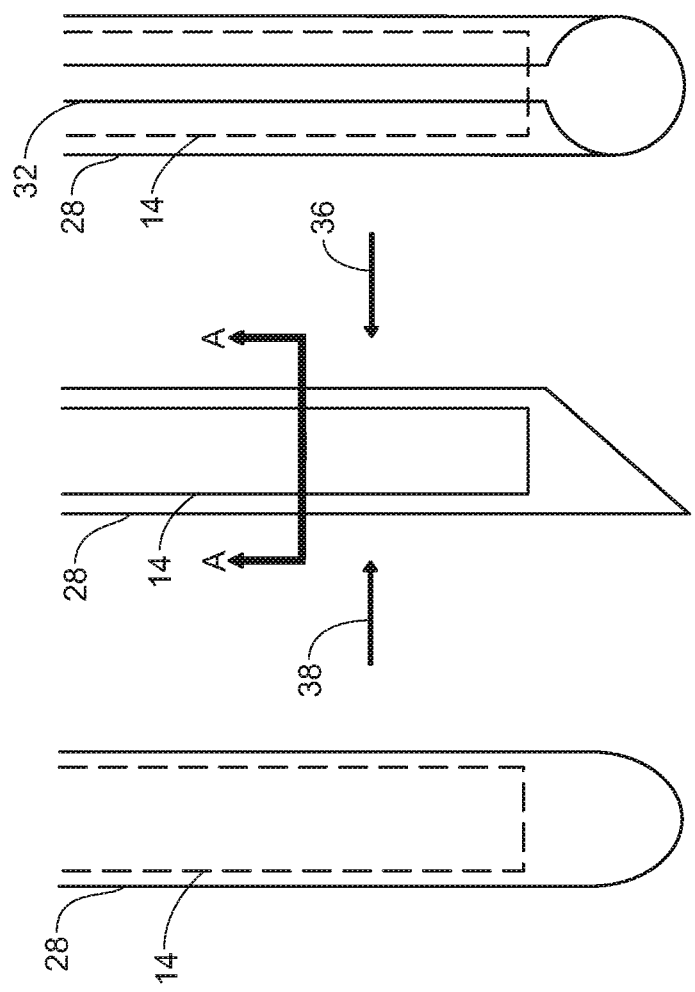

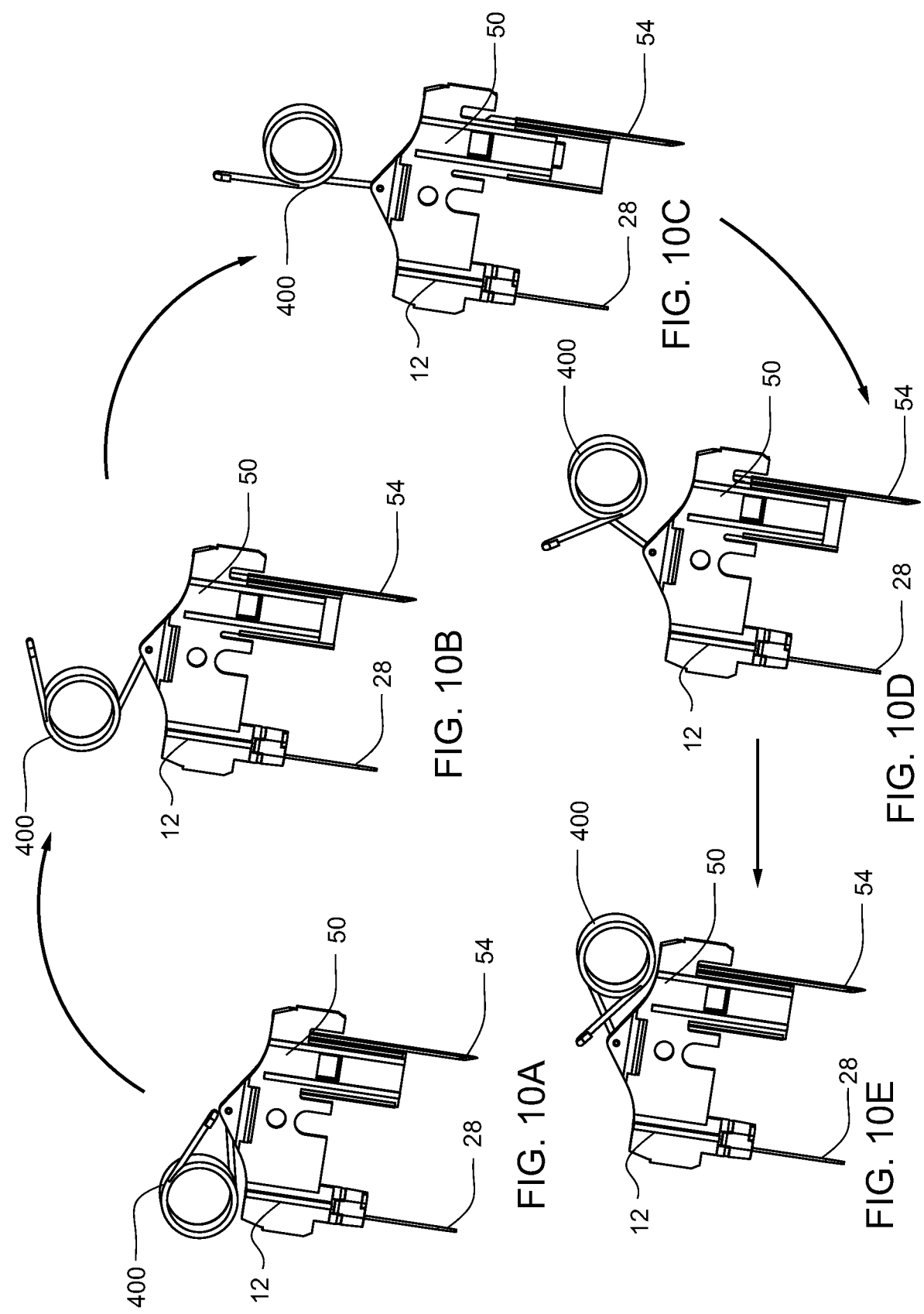

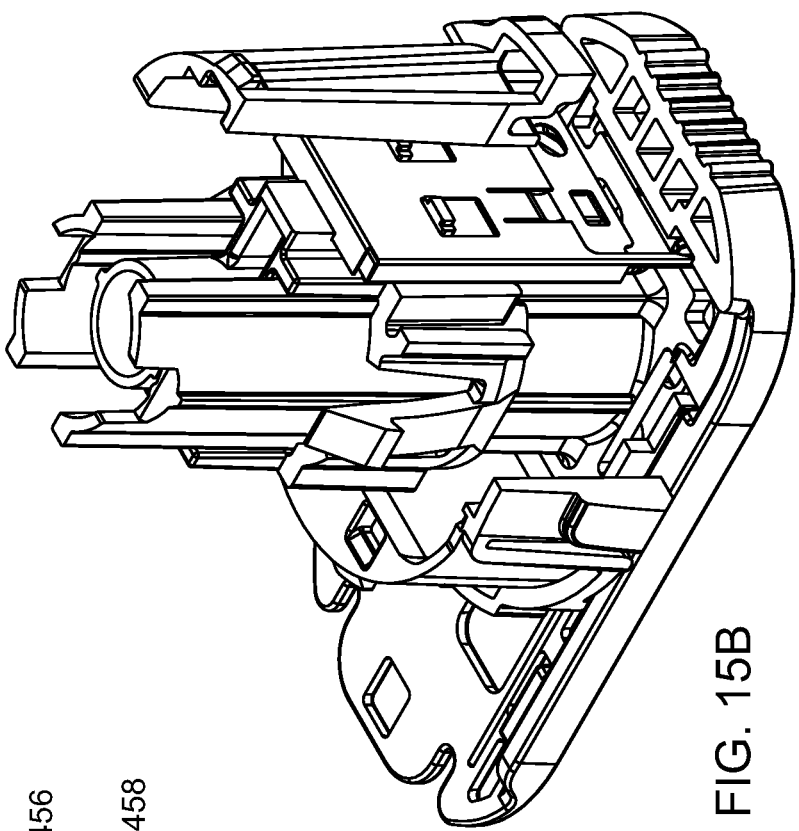
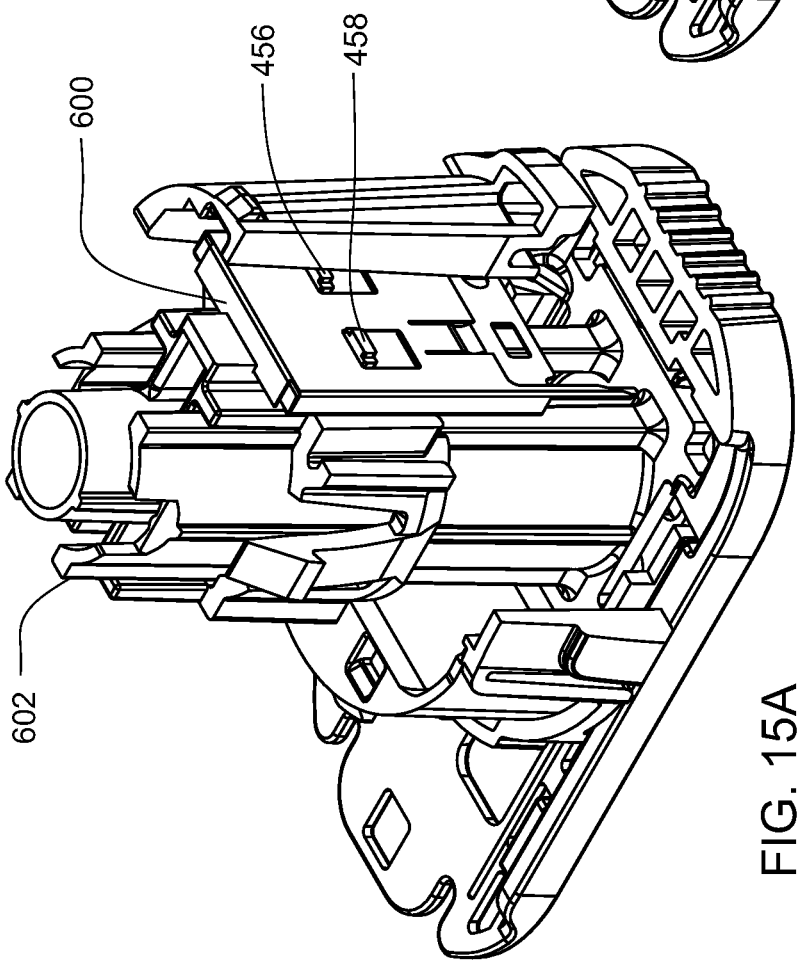
FIG. 15A
FIG. 15B

AUTOMATED INSERTION ASSEMBLY

CROSS REFERENCE TO RELATED APPLICATIONS

The application is a continuation of U.S. patent application Ser. No. 17/222,170, filed Apr. 5, 2021, which is a continuation of U.S. patent application Ser. No. 16/197,773, filed on Nov. 21, 2018, which is a continuation of U.S. patent application Ser. No. 14/840,610, filed on Aug. 31, 2015, which is a continuation of U.S. patent application Ser. No. 13/346,369, filed on Jan. 9, 2012, now U.S. Pat. No. 9,119,913, which is a continuation of U.S. patent application Ser. No. 12/029,234 filed on Feb. 11, 2008, which claims priority to U.S. Provisional Application Ser. No. 60/889,007 filed on Feb. 9, 2007, each of which is hereby incorporated by reference in its entirety.

TECHNICAL FIELD

This disclosure relates to insertion assemblies and, more particularly, to automated insertion assemblies.

BACKGROUND

Numerous devices (e.g., drug delivery systems, analyte monitoring systems, including but not limited to blood glucose monitoring systems or any system monitoring any patient condition from any patient fluid or physiological characteristic) require that the skin of the user being tested be perforated to allow for e.g., the supplying of drug to the user and/or the monitoring of various bodily/physiological conditions (e.g., blood conditions, i.e., glucose levels or other analyte levels whether in the blood or other fluid or indicative by another physical condition, i.e., temperature). The difficulty with these devices is compounded where two or more are used.

Unfortunately, such systems may require the user to manually insert the various cannulas and/or probes into or onto their skin, often resulting in incorrect insertions and discomfort/pain. This problem is compounded when the user is using multiple devices e.g., an insulin delivery system and a blood glucose monitoring system.

SUMMARY OF DISCLOSURE

In a first implementation, an automated insertion assembly includes a first dermal perforation assembly configured to releasably engage a first subdermal device. A first actuation assembly is configured to drive the first dermal perforation assembly into a user's skin to a first depth and drive the first subdermal device into the user's skin to a second depth. The second depth is greater than the first depth.

One or more of the following features may be included. The first subdermal device may be chosen from the group consisting of a cannula assembly and a probe. The first dermal perforation assembly may include a first insertion needle assembly for at least partially encapsulating at least a portion of the first subdermal device. The first actuation assembly may include a first actuator for providing mechanical energy sufficient to drive the first dermal perforation assembly into the user's skin to the first depth and drive the first subdermal device into the user's skin to the second depth. The first actuator may be a spring-based actuator.

The first actuation assembly may include one or more gear assemblies for at least partially coupling the first actuator to the first dermal perforation assembly. The first actuation assembly may include one or more linkage assemblies for at least partially coupling the first actuator to the first dermal perforation assembly.

A second dermal perforation assembly may be configured to releasably engage a second subdermal device. A second actuation assembly may be configured to drive the second dermal perforation assembly into the user's skin to a third depth and drive the second subdermal device into the user's skin to a fourth depth. The fourth depth may be greater than the third depth. The fourth depth may be less than/equal to the third depth.

The second subdermal device may be chosen from the group consisting of a cannula assembly and a probe. The second dermal perforation assembly may include a second insertion needle assembly for at least partially encapsulating at least a portion of the second subdermal device. The second actuation assembly may include a second actuator for providing mechanical energy sufficient to drive the second dermal perforation assembly into the user's skin to the third depth and drive the second subdermal device into the user's skin to the fourth depth.

The second actuator may be a spring-based actuator. The second actuation assembly may include one or more gear assemblies for at least partially coupling the second actuator to the second dermal perforation assembly. The second actuation assembly may include one or more linkage assemblies for at least partially coupling the second actuator to the second dermal perforation assembly. The first actuation assembly and the second actuation assembly may be a single actuation assembly.

In another implementation, an automated insertion assembly includes a first dermal perforation assembly configured to releasably engage a first subdermal device. A second dermal perforation assembly is configured to releasably engage a second subdermal device. An actuation assembly is configured to: drive the first dermal perforation assembly into a user's skin to a first depth, drive the first subdermal device into the user's skin to a second depth, drive the second dermal perforation assembly into the user's skin to a third depth, and drive the second subdermal device into the user's skin to a fourth depth. The second depth is greater than the first depth.

One or more of the following features may be included. The fourth depth may be greater than the third depth. The fourth depth may be less than/equal to the third depth. The first subdermal device and the second subdermal device may be chosen from the group consisting of a cannular assembly and a probe.

The first dermal perforation assembly may include a first insertion needle assembly for at least partially encapsulating at least a portion of the first subdermal device. The second dermal perforation assembly may include a second insertion needle assembly for at least partially encapsulating at least a portion of the second subdermal device. The actuation assembly may include an actuator for providing mechanical energy sufficient to drive the first dermal perforation assembly into a user's skin to a first depth, drive the first subdermal device into the user's skin to a second depth, drive the second dermal perforation assembly into the user's skin to a third depth, and drive the second subdermal device into the user's skin to a fourth depth. The actuator may be a spring-based actuator.

In another implementation, an automated insertion assembly includes a first dermal perforation assembly configured to releasably engage a first subdermal device, a second subdermal device, and an actuation assembly. The actuation assembly is configured to: drive the first dermal perforation assembly into a user's skin to a first depth, drive the first subdermal device into the user's skin to a second depth, and drive the second subdermal device into the user's skin to a third depth. The second depth is greater than the first depth.

One or more of the following features may be included. The second subdermal device may be a cannula assembly. The first dermal perforation assembly may include a first insertion needle assembly for at least partially encapsulating at least a portion of the first subdermal device. The actuation assembly may include an actuator for providing mechanical energy sufficient to drive the first dermal perforation assembly into a user's skin to a first depth, drive the first subdermal device into the user's skin to a second depth, and drive the second subdermal device into the user's skin to a third depth.

The details of one or more implementations are set forth in the accompanying drawings and the description below. Other features and advantages will become apparent from the description, the drawings, and the claims.

BRIEF DESCRIPTION OF THE DRAWINGS

FIGS. 3, 3L, 3R, and 3T are diagrammatic views of an insertion needle assembly of the automated insertion assembly of FIG. 1;

FIGS. 10A-10E are diagrammatic views of a spring-based actuator of the automated insertion assembly of FIG. 1;

FIGS. 15A-15L are a series of views of an alternative embodiment of the automated insertion assembly of FIG. 1.

Like reference symbols in the various drawings indicate like elements.

DETAILED DESCRIPTION OF EXEMPLARY EMBODIMENTS

Figure 1:
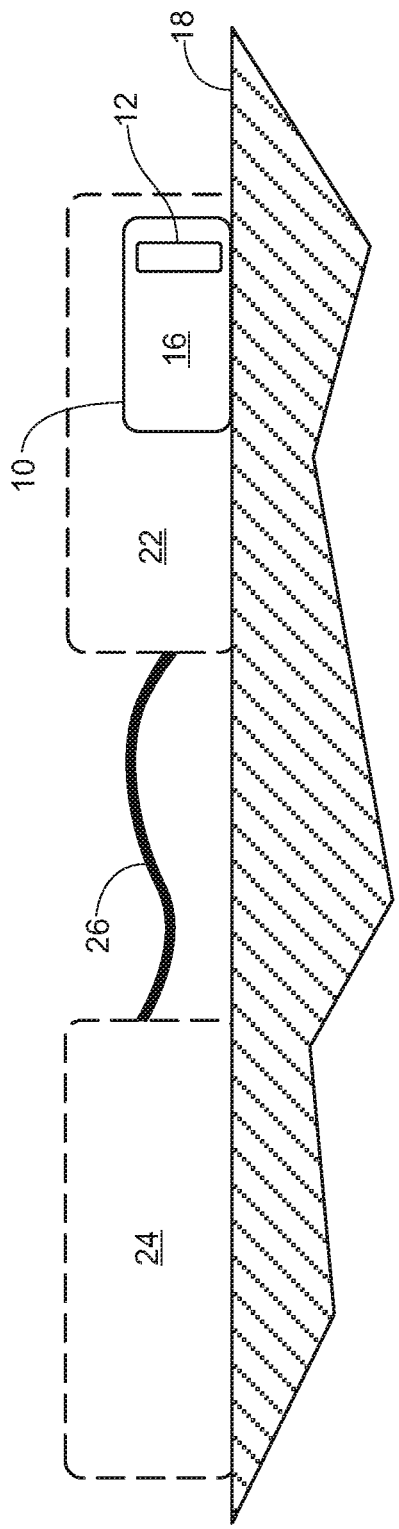
FIG. 1 is a diagrammatic view of an automated insertion assembly.

The following description describes various embodiments of an automated insertion assembly. The device is a mechanical device capable of automatically inserting or introducing one or more probes or sensors. In one embodiment, the device includes automatically inserting at least one probe into a patient's skin by first inserting an introduction needle that at least partially encapsulates the probe. The insertion needle reaches a predetermined first depth in the skin and is withdrawn by the device, leaving the probe behind. The device additionally includes a pusher device that automatically and mechanically pushes the probes to a second depth, deeper than the first depth. The pusher device is then mechanically and automatically retracted.

In another embodiment, in addition to the probe insertion capabilities described above, the inerter apparatus additionally includes a cannula or other drug delivery insertion device. The cannula insertion device includes an automatic and mechanical inserter that inserts a cannula using an introduction needle. The insertion needle is automatically and mechanically retracted.

In one embodiment of the apparatus, both the cannula and probe are inserted simultaneously. The probe inserter includes a pusher where the cannula inserter does not. However, the introduction needles perforate the skin simultaneously.

Inserting two devices at the same time has many advantages, including but not limited to, convenience and less pain and/or less number of painful events for the patient. Additionally, because both devices are inserted using the same apparatus, the spacing between the two devices in the patient can be predetermined and thus, may increase accuracy, efficiency and safety in the use of the devices. For example, in some applications, the inserter is used to insert two or more probes or other devices; at appropriate distances one from another. However, in other applications where a probe and delivery device are inserted together, the probes or probe and delivery device should be spaced apart a minimum distance for accuracy. Inserting both devices using the same inserter assures the patient inserts both devices at the minimum recommended distance. Additionally, in some embodiments, the inserter may apply two or more sensors or probes at a predetermined distance, where the readings between the sensors or probes are indicative. In these embodiments, the distance between the probes or sensors is maintained for accuracy and/or to eliminate or minimize interference. Thus, again, in this instance, the inserter assures the correct distance.

In another embodiment, the inserter inserts two or more probes, two or more sensors or two or more cannulas or drug delivery devices simultaneously. In still further embodiments, the inserter may insert a variety of sensors or probes or all the same sensors or probes and/or drug delivery paths, cannulas or needles.

Referring to FIGS. 1, 2, 3, 3L, 3R & 3T, there is shown automated insertion assembly 10 that may include first dermal perforation assembly 12 that may be configured to releasably engage first subdermal device 14. First actuation assembly 16 may be configured to drive first dermal perforation assembly 12 into a user's skin 18 to a first depth and drive first subdermal device 14 into user's skin 18 to a second depth. The manner in which automated insertion assembly 10 drives first dermal perforation assembly 12 to a first depth and drives first subdermal device 14 to a second depth is described below in greater detail. Typically, the second depth (i.e. the depth to which first subdermal device 14 is driven) is greater than the first depth (i.e. the depth to which first dermal perforation assembly 12 is driven), thus allowing first subdermal device 14 to penetrate skin that was not previously penetrated/damaged by first dermal perforation assembly 12. However, the second depth in some embodiments may be equal or less than the first depth.

Examples of first subdermal device 14 may include but are not limited to a cannula assembly, a needle assembly, an infusion assembly, a glucose monitoring probe, a potassium or any electrolyte and/or analyte monitoring probe, or any type of probe that monitors any chemical, analyte or physiological characteristic including, but not limited to, hydration and/or temperature and/or conductivity/electrical pulses. In still other embodiments, the probes may impart an electrical stimulation. Additionally, in some embodiments, the device may include an RF transmitter or compounds. In one embodiment, the compound is any therapeutic compound, and dissolves into the dermal layer over a period of time. In still other embodiments, the device may include, but is not limited to, a bedside IV or other patient monitoring assembly, or any other device used to monitor physiological conditions.

Automated insertion assembly 10 may be included within (or a portion of) various other devices (e.g., device 22), examples of which may include but are not limited to an infusion pump assembly, a glucose monitoring system, a potassium or any electrolyte monitoring system, an analyte monitoring system or any type of system or device that monitors any chemical or physiological characteristic including, but not limited to, hydration and/or temperature and/or conductivity. In still other embodiments, the probes may impart an electrical stimulation and may be part of an electrical stimulation device. Additionally, in some embodiments, the device may include an RF transmitter or compounds. In one embodiment, the compound is any therapeutic compound system, and in one embodiment, the system provides for a compound that dissolves into the dermal layer over a period of time. In still other embodiments, the device may include, but is not limited to, a bedside IV or other patient monitoring assembly, or any other device used to monitor physiological conditions. Further, automated insertion assembly 10 may be separate from (but tethered to) various other devices (e.g. device 24), examples of which may include but are not limited to an infusion pump assembly, a glucose monitoring system or probe, a potassium or any electrolyte monitoring system or probe, or any type of probe or system that monitors any chemical, analyte or physiological characteristic including, but not limited to, hydration and/or temperature. Additionally, in some embodiments, the device may include an RF transmitter or compounds. In one embodiment, the compound is any therapeutic compound, and dissolves into the dermal layer over a period of time. In still other embodiments, the device may include, but is not limited to, a bedside IV or other patient monitoring assembly, or any other device used to monitor physiological conditions.

First dermal perforation assembly 12 may include first insertion needle assembly 28 that may be configured to at least partially encapsulate at least a portion of first subdermal device 14. However, in some embodiments, an insertion needle assembly is not included.

First actuation assembly 16 may include first actuator 30 for providing mechanical energy sufficient to drive first dermal perforation assembly 12 into user's skin 18 to the first depth and drive first subdermal device 14 into user's skin 18 to the second depth. Examples of first actuator 30 may include but are not limited to a spring-based actuator (not shown), a motor-based actuator (not shown), a pneumatic-based actuator (not shown), and a shape memory wire-based actuator (not shown).

First actuation assembly 16 may include one or more gear assemblies (to be discussed below in greater detail) for at least partially coupling first actuator 30 to first dermal perforation assembly 12. Additionally/alternatively, first actuation assembly 16 may include one or more linkage assemblies (to be discussed below in greater detail) for at least partially coupling first actuator 30 to first dermal perforation assembly 12.

First insertion needle assembly 28 of first dermal perforation assembly 12 may be configured to allow first subdermal device 14 to exit from first insertion needle assembly 28. For example, first insertion needle assembly 28 may include longitudinal slot 32 through which first subdermal device 14 may exit from first insertion needle assembly 28. Specifically, first insertion needle assembly 28 may be a traditional hypodermic-type (i.e. hollow core) needle assembly. As shown in FIG. 3T (which is a cross-sectional view of FIG. 3 along section line AA), first insertion needle assembly 28 may include interior passage 34 which may be sized to receive first subdermal device 14. As shown in FIG. 3R (i.e. a right-side view of first insertion needle assembly 28 in the direction of arrow 36) and FIG. 3L (i.e. a left-side view of first insertion needle assembly 28 in the direction of arrow 38), longitudinal slot 32 may extend the entire length of first insertion needle assembly 28. Alternatively, longitudinal slot 32 may extend a partial length of first insertion needle assembly 28, wherein the partial length is positioned to allow first subdermal device 14 to exit first insertion needle assembly 28 at the appropriate position along the length of first insertion needle assembly 28.

Figure 4:
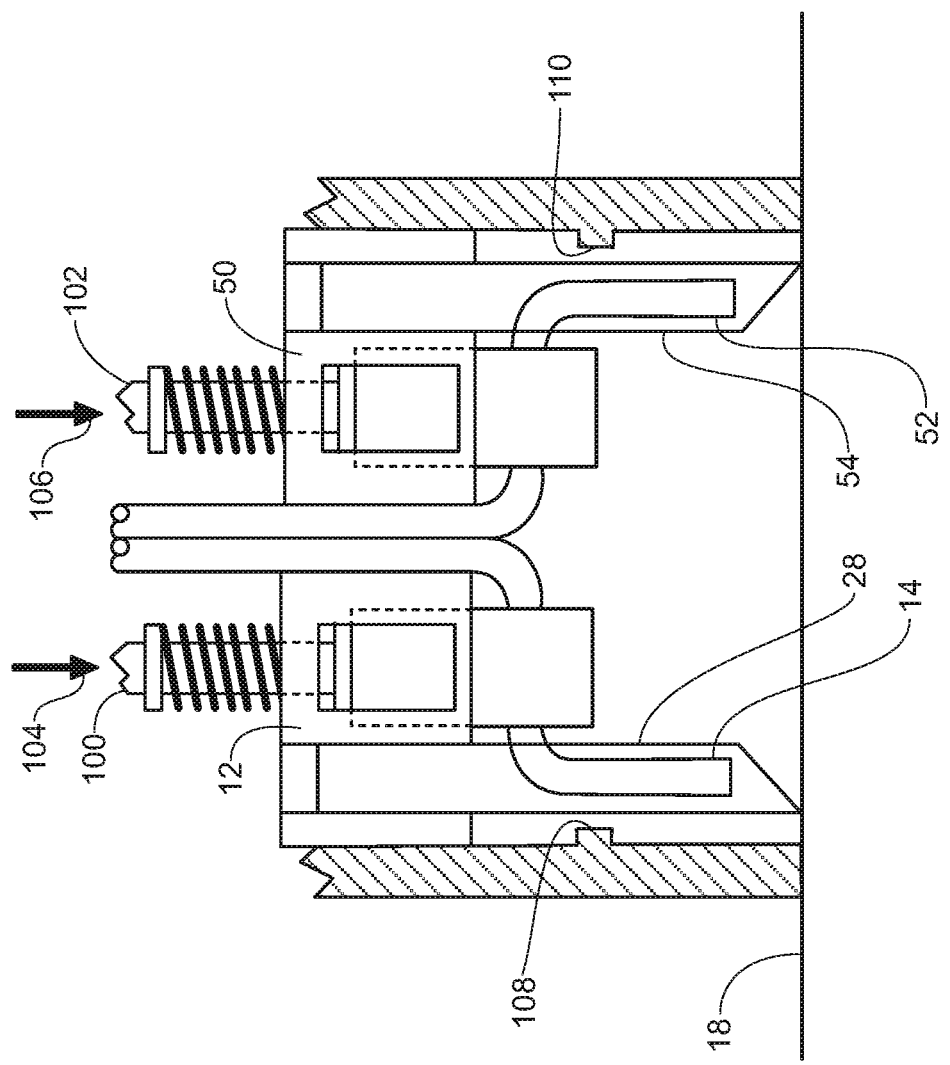
FIG. 4 is another diagrammatic view of the automated insertion assembly of FIG. 1.

Referring to FIG. 4, automated insertion assembly 10 may include second dermal perforation assembly 50. Second dermal perforation assembly 50 may be configured to releasably engage second subdermal device 52. A second actuation assembly (not shown) may be configured to drive second dermal perforation assembly 50 into user's skin 18 to a third depth and drive second subdermal device 52 into user's skin 18 to a fourth depth. This second actuation assembly (not shown) may include a second actuator for providing the mechanical energy sufficient to drive second dermal perforation assembly 50 into user's skin 18 to the third depth and drive second subdermal device 52 into user's skin 18 to the fourth depth. Examples of this second actuator (not shown) may include but are not limited to a spring-based actuator (not shown), a motor-based actuator (not shown), a pneumatic-based actuator (not shown), and a shape memory wire-based actuator (not shown).

In alternate embodiments of automated insertion assembly 10, the various dermal perforation assemblies may be configured such that one or more are driven to equal depths. In one embodiment, all of the assemblies are driven to equal depths.

In a fashion similar to that of first actuation assembly 16, the second actuation assembly (not shown) may include one or more gear assemblies (to be discussed below in greater detail) for at least partially coupling the second actuator (not shown) to second dermal perforation assembly 50. Additionally/alternatively, the second actuation assembly (not shown) may include one or more linkage assemblies (to be discussed below in greater detail) for at least partially coupling the second actuator (not shown) to second dermal perforation assembly 50.

Alternatively, first dermal perforation assembly 12 and second dermal perforation assembly 50 may be driven by a common actuation assembly (e.g. first actuation assembly 16) and/or a common actuator (e.g. first actuator 30).

Typically, the fourth depth (i.e. the depth to which second subdermal device 52 is driven) is greater than the third depth (i.e. the depth to which second dermal perforation assembly 50 is driven), thus allowing a second subdermal device 52 to penetrate skin that was not previously penetrated/damaged by second dermal perforation assembly 50.

The third depth (i.e. the depth to which second dermal perforation assembly 50 is driven) may be the same as or different from the first depth (i.e. the depth to which first dermal perforation assembly 12 is driven). Further, the fourth depth (i.e. the depth to which second subdermal device 52 is driven) may be the same as or different from the first depth (i.e. the depth to which first subdermal device 14 is driven).

In a fashion similar to that of first subdermal device 14, examples of second subdermal device 52 may include but are not limited to a cannula assembly, a glucose monitoring probe, a potassium or any electrolyte monitoring probe, or any type of probe that monitors any chemical, analyte or physiological characteristic including, but not limited to, hydration and/or temperature. Additionally, in some embodiments, the device may include an RF transmitter or compounds. In one embodiment, the compound is any therapeutic compound, and dissolves into the dermal layer over a period of time. In still other embodiments, the device may include, but is not limited to, a bedside IV or other patient monitoring assembly, or any other device used to monitor physiological conditions.

In a fashion similar to that of first dermal perforation assembly 12, second dermal perforation assembly 50 may include second insertion needle assembly 54 that may be configured to at least partially encapsulate at least a portion of second subdermal device 52. Second insertion needle assembly 54 of second dermal perforation assembly 50 may be configured to allow second subdermal device 52 to exit second insertion needle assembly 54. For example, second insertion needle assembly 54 may include a longitudinal slot (similar to that of first insertion needle assembly 28) through which second subdermal device 52 may exit second insertion needle assembly 54.

As discussed above, in one embodiment, first dermal perforation assembly 12 may be driven into user's skin 18 to a first depth; first subdermal device 14 may be driven into user's skin 18 to a second depth; second dermal perforation assembly 50 may be driven into user's skin 18 to a third depth; and second subdermal device 52 may be driven into user's skin 18 to a fourth depth. However, in other embodiments, first dermal perforation assembly 12 and/or any one or more of the subdermal devices 14, 52 may be ultimately driven to the same depths. Thus, herein, the terms first depth, second depth, etc., may mean different depths or the same depth, depending on the embodiment. However, it should be appreciated that automated insertion assembly 10 allows one or more devices to be inserted at the same or different depth.

Thus, automated insertion assembly 10 may be configured to drive first dermal perforation assembly 12 to a first depth; drive first subdermal device 20 to a second depth; drive second dermal perforation assembly 50 to a third depth; and drive second subdermal device 52 to a fourth depth, in a variety of different ways, each of which is considered to be within the scope of this disclosure.

Accordingly and for illustrative purposes only, a first configuration is illustrated in FIGS. 4-8. As shown in FIG. 4, first actuation assembly 16 (and/or a second actuation assembly, not shown) may displace linkage assembly 100 and/or linkage assembly 102 in the direction of arrows 104, 106 (respectively). Linkage assemblies 100, 102 may be coupled to one or more gear assemblies coupled to e.g., first actuator 30. For example, if actuator 30 is a motor, an output shaft (not shown) of actuator 30 may include a gear assembly (not shown) to e.g., mesh with a rack gear assembly (not shown) included within e.g., linkage assembly 100, thus allowing for the conversion of rotational energy into linear displacement.

The displacement of linkage assembly 100 and/or linkage assembly 102 may result in first dermal perforation assembly 12 (and first insertion needle assembly 28) and/or second dermal perforation assembly 50 (and second insertion needle assembly 54) moving toward user's skin 18. Automated insertion assembly 10 may include one or more depth stops (e.g., depth stops 108, 110) for controlling the total displacement experienced by first dermal perforation assembly 12 and/or second dermal perforation assembly 50.

The positioning of depth stops 108, 110 is for illustrative purposes only and is not intended to be a limitation of this disclosure. For example, depth stops 108, 110 may be positioned lower or higher within automated insertion assembly 10, or first dermal perforation assembly 12 and/or second dermal perforation assembly 50 may be configured to "bottom out" on the surface of user's skin 18.

Figure 5:
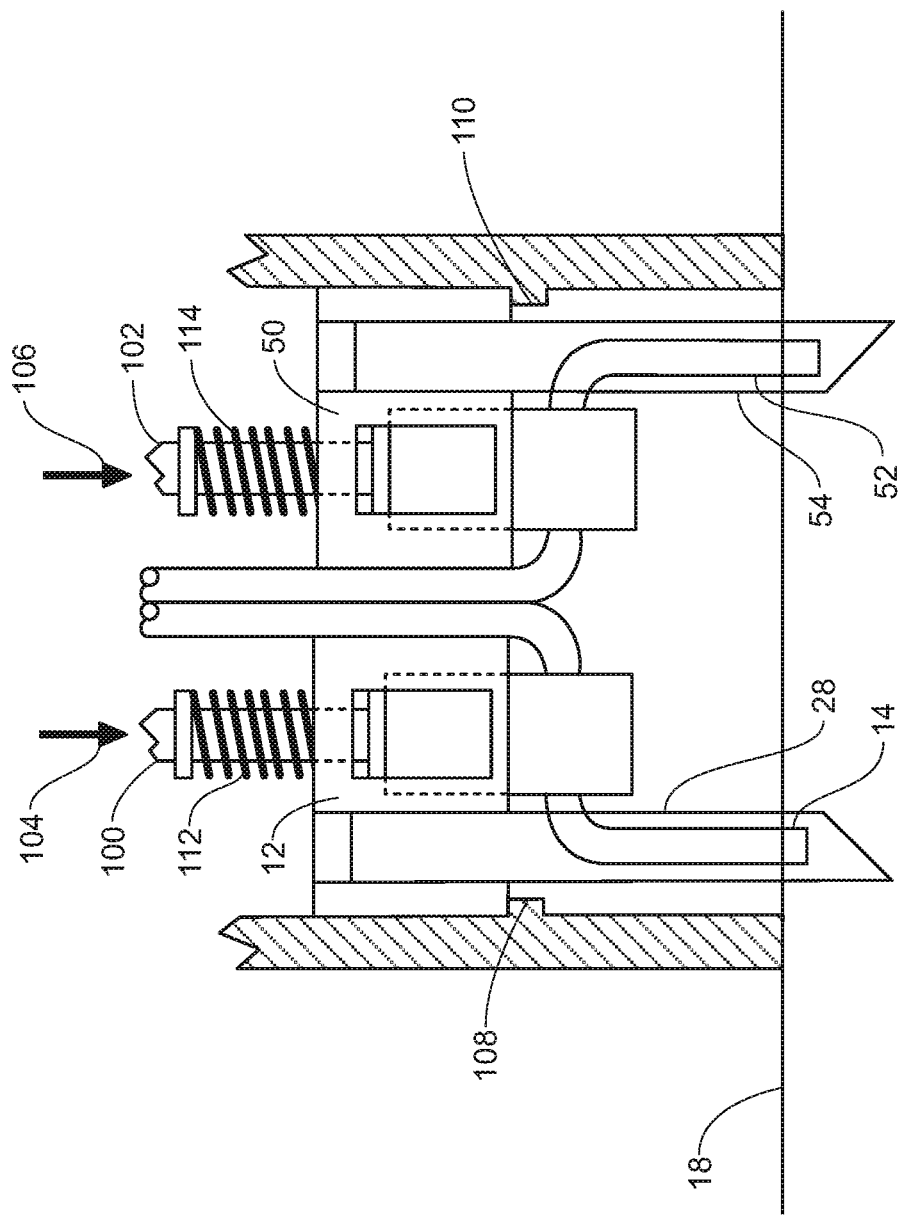
FIG. 5 is another diagrammatic view of the automated insertion assembly of FIG. 1.

Referring also to FIG. 5, first dermal perforation assembly 12 and/or second dermal perforation assembly 50 may continue to move downward until (in this particular example) first dermal perforation assembly 12 contacts depth stop 108 and/or second dermal perforation assembly 50 contacts depth stop 110. Once depth stop 108 and/or depth stop 110 contacts first dermal perforation assembly 12 and/or second dermal perforation assembly 50, one or more spring assemblies (e.g. spring assembly 112 and/or spring assembly 114) may begin to compress. Specifically, spring assembly 112 and/or spring assembly 114 may be sized to provide a mechanical resistance that is sufficient to drive first insertion needle assembly 28 (included within first dermal perforation assembly 12) and/or second insertion needle assembly 54 (included within second dermal perforation assembly 50) into user's skin 18.

The positioning of spring assemblies 112, 114 is for illustrative purposes only and is not intended to be a limitation of this disclosure. For example, spring assemblies 112, 114 may be positioned lower within automated insertion assembly 10 to reduce the overall height of automated insertion assembly 10.

Figure 6:
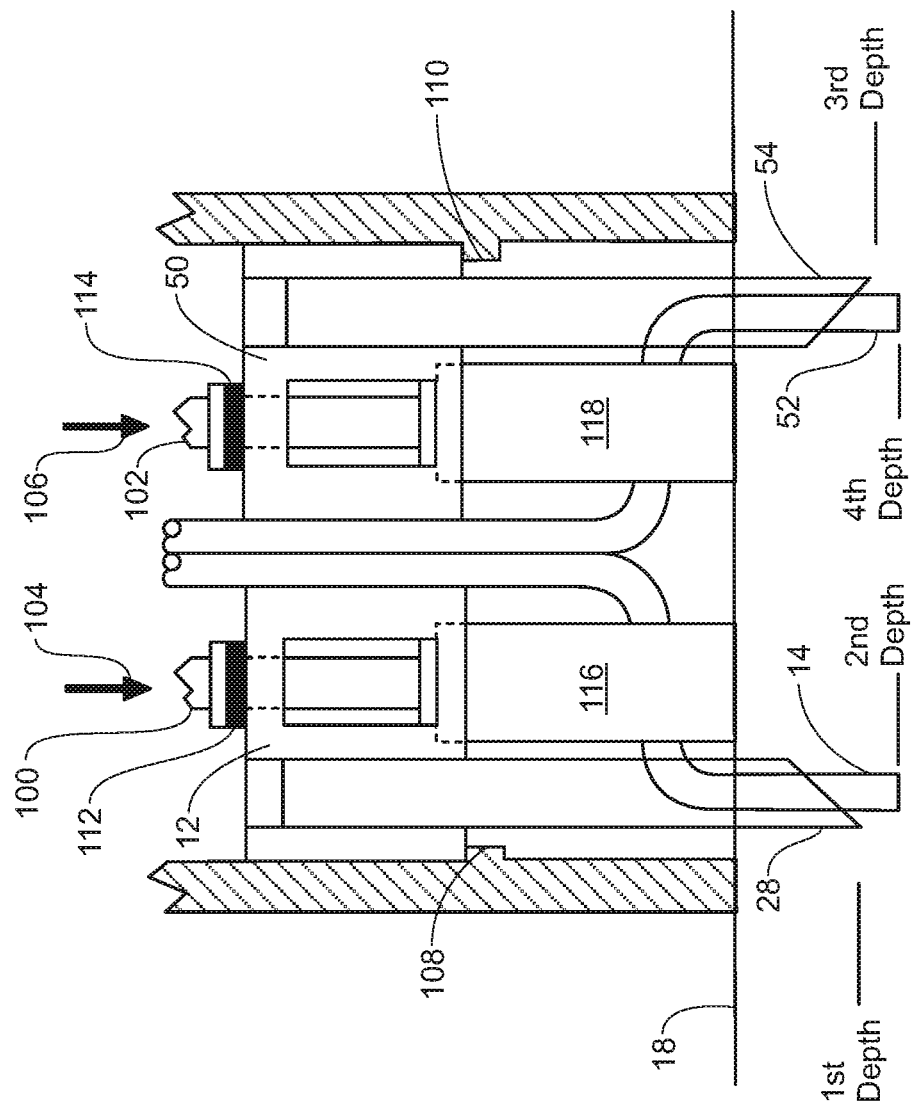
FIG. 6 is another diagrammatic view of the automated insertion assembly of FIG. 1.

Referring also to FIG. 6, spring assembly 112 and/or spring assembly 114 may continue to compress. Further, in this particular example, linkage assembly 100 is shown to be directly coupled to a portion (e.g., portion 116) of first subdermal device 14. Depth stop 108 may be positioned to allow linkage assembly 100 to drive first dermal perforation assembly 12 to the above-described first depth.

Accordingly, once depth stop 108 is encountered by first dermal perforation assembly 12, all downward movement of first dermal perforation assembly 12 may cease. However, as spring assembly 112 compresses, linkage assembly 100 may continue to move in a downward direction. Further, as first subdermal device 14 is (in this particular example) directly coupled to linkage assembly 100 (via portion 116), first subdermal device 14 may continue to move in a downward direction, continuing to penetrate user's skin 18 to a depth (e.g., the above-described second depth) that is deeper than the depth of first insertion needle assembly 28 of first dermal perforation assembly 12 (e.g., the above-described first depth).

Portion 116 of first subdermal device 14 may e.g. contain electronic circuitry and/or sensing devices that process the data obtained by first subdermal device 14. Alternatively, portion 116 of first subdermal device 14 may simply be a rigid device upon which linkage assembly 100 may provide downward pressure to drive first subdermal device 14 to the above-described second depth.

At least a portion of first subdermal device 14 (e.g. the portion penetrating user's skin 18) may be constructed of a material that is sufficiently rigid to penetrate user's skin 18. Examples of such a material may include but are not limited to steel, stainless steel, titanium, or plastic. Accordingly, when linkage assembly 100 continues to provide downward force (in the direction of arrow 104), first subdermal device 14 may continue to penetrate user's skin 18 until the desired depth (e.g., the above-described second depth) is achieved. While the above-described first depth (i.e., the depth of first insertion needle 28 of first dermal perforation assembly 12) may be adjusted by adjusting (in this example) the position of depth stop 108), the above-described second depth (i.e., the depth of first subdermal device 14) may be adjusted by adjusting the total travel of linkage assembly 100.

Additionally and in this particular example, linkage assembly 102 is shown to be directly coupled to a portion (e.g., portion 118) of second subdermal device 52. Depth stop 110 may be positioned to allow linkage assembly 102 to drive second dermal perforation assembly 50 to the above-described third depth.

Accordingly, once depth stop 110 is encountered by second dermal perforation assembly 50, all downward movement of second dermal perforation assembly 50 may cease. However, as spring assembly 114 compresses, linkage assembly 102 may continue to move in a downward direction. Further, as second subdermal device 52 is (in this particular example) directly coupled to linkage assembly 102 (via portion 118), second subdermal device 52 may continue to move in a downward direction, continuing to penetrate user's skin 18 to a depth (e.g., the above-described fourth depth) that is deeper than the depth of second insertion needle assembly 54 of second dermal perforation assembly 50 (e.g., the above-described third depth).

Portion 118 of second subdermal device 52 may e.g. contain electronic circuitry and/or sensing devices that process the data obtained by second subdermal device 52. Alternatively, portion 118 of second subdermal device 52 may simply be a rigid device upon which linkage assembly 102 may provide downward pressure to drive second subdermal device 52 to the above-described fourth depth.

At least a portion of second subdermal device 52 (e.g. the portion penetrating user's skin 18) may be constructed of a material that is sufficiently rigid to penetrate user's skin 18. Examples of such a material may include but are not limited to steel, stainless steel, titanium, or plastic. Accordingly, when linkage assembly 102 continues to provide downward force (in the direction of arrow 106), second subdermal device 52 may continue to penetrate user's skin 18 until the desired depth (e.g., the above-described fourth depth) is achieved. While the above-described third depth (i.e., the depth of second insertion needle 54 of second dermal perforation assembly 50) may be adjusted by adjusting (in this example) the position of depth stop 110), the above-described fourth depth (i.e., the depth of second subdermal device 52) may be adjusted by adjusting the total travel of linkage assembly 102.

Figure 7:
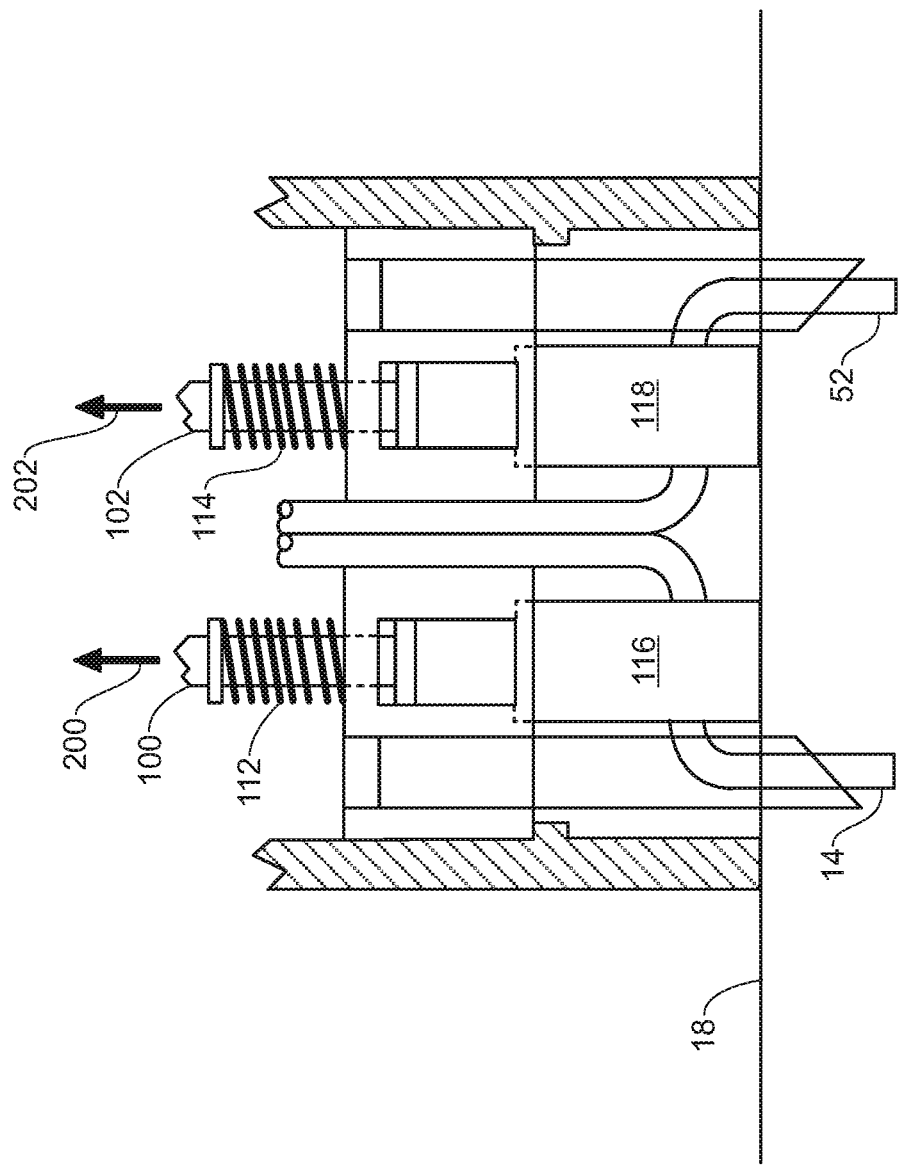
FIG. 7 is another diagrammatic view of the automated insertion assembly of FIG. 1.

Continuing with the above-stated example and referring also to FIG. 7, upon achieving the desired depth (i.e. the above-described second depth for first subdermal device 14 and/or the above-described fourth depth for second subdermal device 52), linkage assembly 100 and/or linkage assembly 102 may begin to move upward in the direction of arrow 200 and/or arrow 202. Accordingly, spring assembly 112 and/or spring assembly 114 may decompress. As linkage assembly 100 and/or linkage assembly 102 move in an upward direction, linkage assembly 100 and/or linkage assembly 102 may move away from portion 116 of first subdermal device 14 and/or portion 118 of second subdermal device 52. Accordingly, while linkage assembly 100 and/or linkage assembly 102 move upward, first subdermal device 14 and or second subdermal device 52 may remain within user skin 18.

Figure 8:
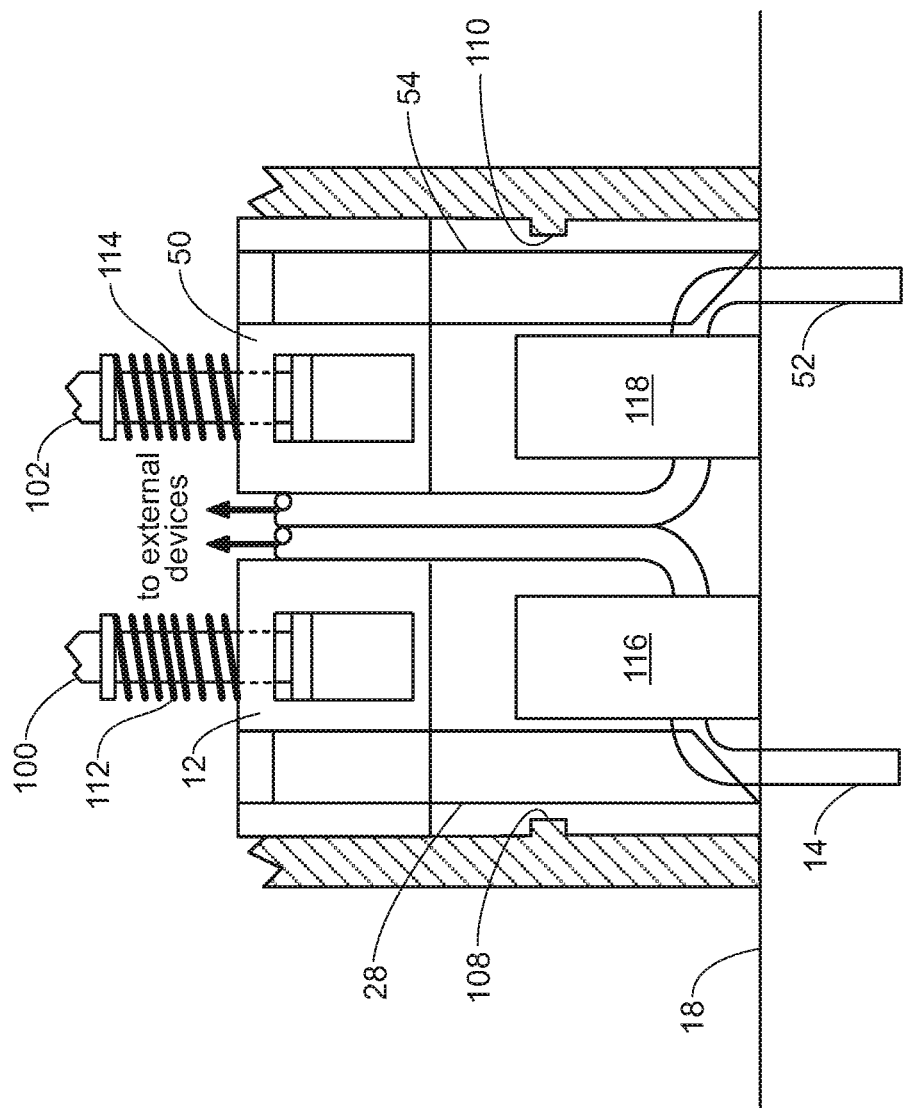
FIG. 8 is another diagrammatic view of the automated insertion assembly of FIG. 1.

Referring also to FIG. 8, once spring assembly 112 and/or spring assembly 114 are fully decompressed, first dermal perforation assembly 12 and/or second dermal perforation assembly 50 may begin to move upward (i.e. away from depth stops 108, 110 respectively). Accordingly, first insertion needle assembly 28 of first dermal perforation assembly 12 may also move upward and may be removed from user's skin 18. Further, second insertion needle assembly 54 of second dermal perforation assembly 50 may also move upward and may be removed from user's skin 18.

As discussed above, automated insertion assembly 10 may be configured to drive first dermal perforation assembly 12 to a first depth; drive first subdermal device 14 to a second depth; drive second dermal perforation assembly 50 to a third depth; and drive second subdermal device 52 to a fourth depth, in a variety of different ways, each of which is considered to be within the scope of this disclosure. Accordingly, while FIGS. 4-8 illustrates a single linkage assembly (e.g. linkage assembly 100), wherein each linkage assembly utilizes a spring assembly (e.g. spring assembly 112) to allow e.g. first subdermal device 14 to be inserted into user's skin 18 at a depth greater than that of first insertion needle assembly 28 of first dermal perforation assembly 12, other configurations are possible and are considered to be within the scope of this disclosure.

Figure 9A:
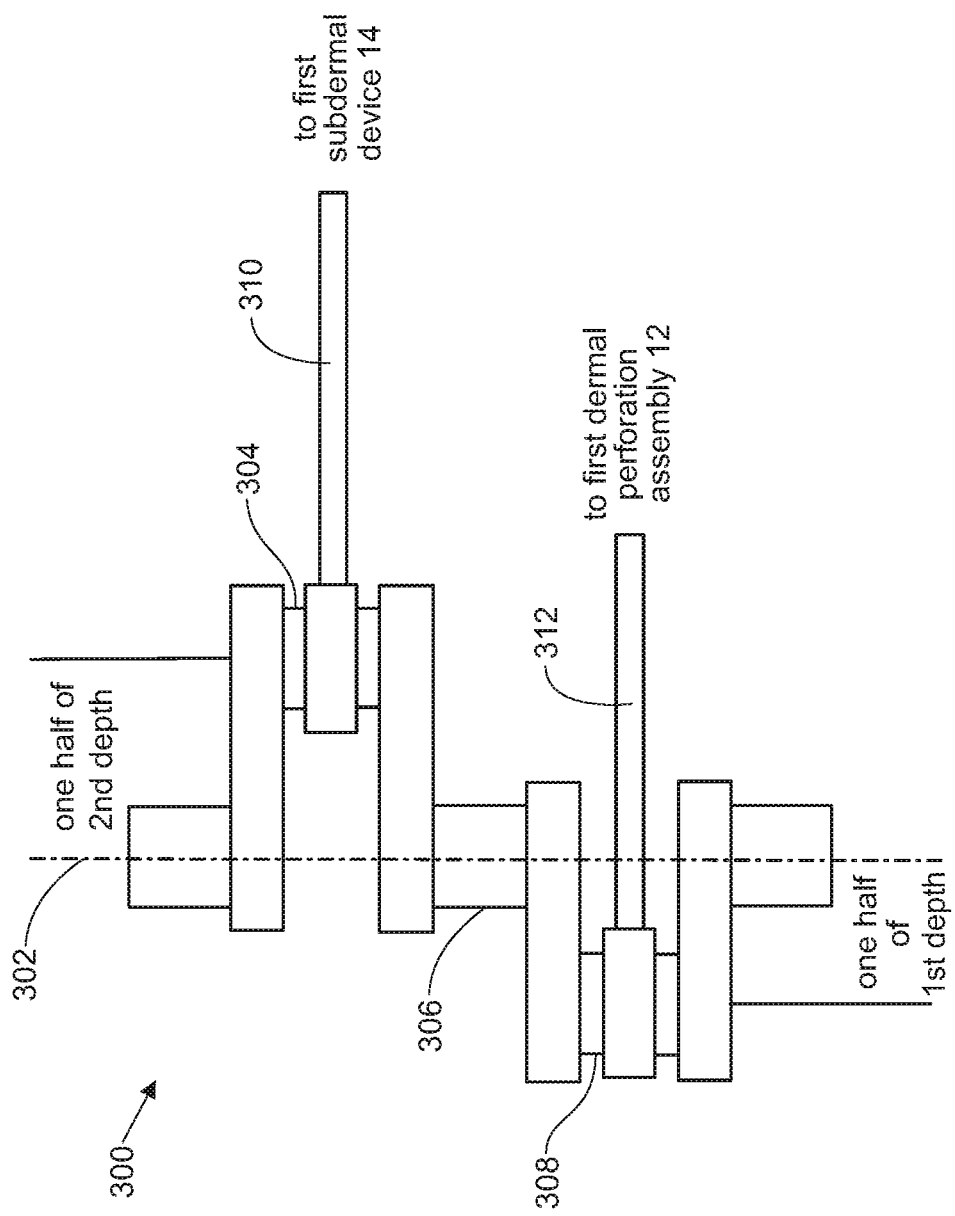
FIG. 9A is a diagrammatic view of a crank assembly of the automated insertion assembly of FIG. 1.

For example and referring also to FIG. 9A, an actuator (e.g. actuator 30) included within an actuation assembly (e.g. actuation assembly 16) may be configured to rotate crank assembly 300, which rotates about centerline 302. Crank assembly 300 may be configured as a variable stroke crank assembly. For example, first rod journal 304 may be offset (with respect to main journal 306) by a distance of 50% of the second depth and second rod journal 308 may be offset (with respect to main journal 306) by a distance of 50% of the first depth. Linkage assembly 310 (e.g., a connecting rod) may be coupled to rod journal 304 and configured to drive first subdermal device 14 and linkage assembly 312 (e.g., a connecting rod) may be coupled to rod journal 308 and configured to drive first dermal perforation assembly 12. Accordingly, as crank assembly 300 rotates about centerline 302, linkage assembly 310 is linearly displaced the distance required to achieve the above-described second depth and linkage assembly 312 is linearly displaced the distance required to achieve the above-described first depth.

Figure 9B:
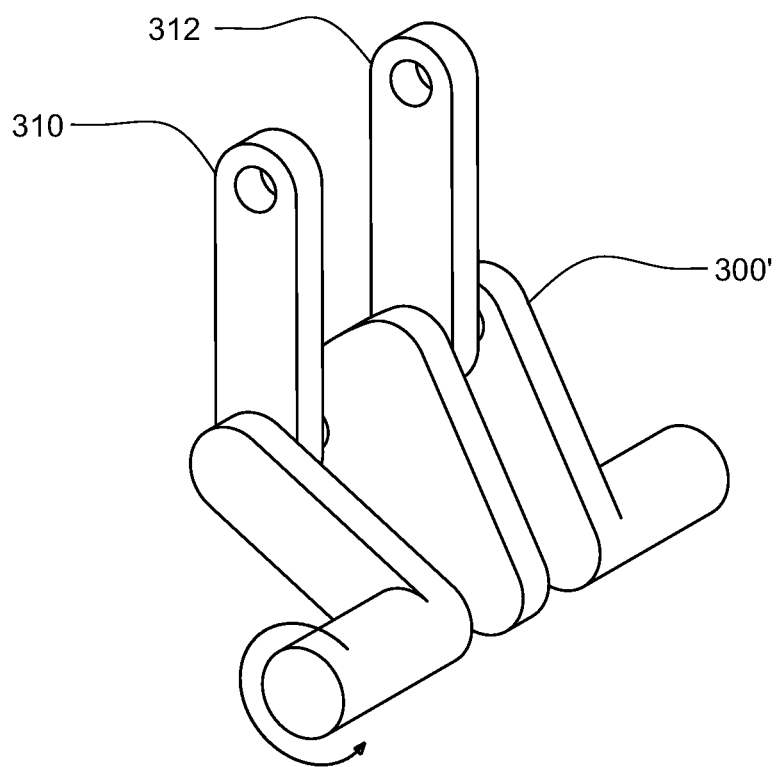
FIG. 9B is a diagrammatic view of an alternative embodiment of the crank assembly of FIG. 9A.

Referring also to FIG. 9B, an alternative crank assembly 300' is shown. As with crank assembly 300, crank assembly 300' may be configured as a variable stroke crank assembly. Accordingly, as crank assembly 300' rotates, linkage assembly 310 is linearly displaced the distance required to achieve the above-described second depth and linkage assembly 312 is linearly displaced the distance required to achieve the above-described first depth.

Figure 9C:
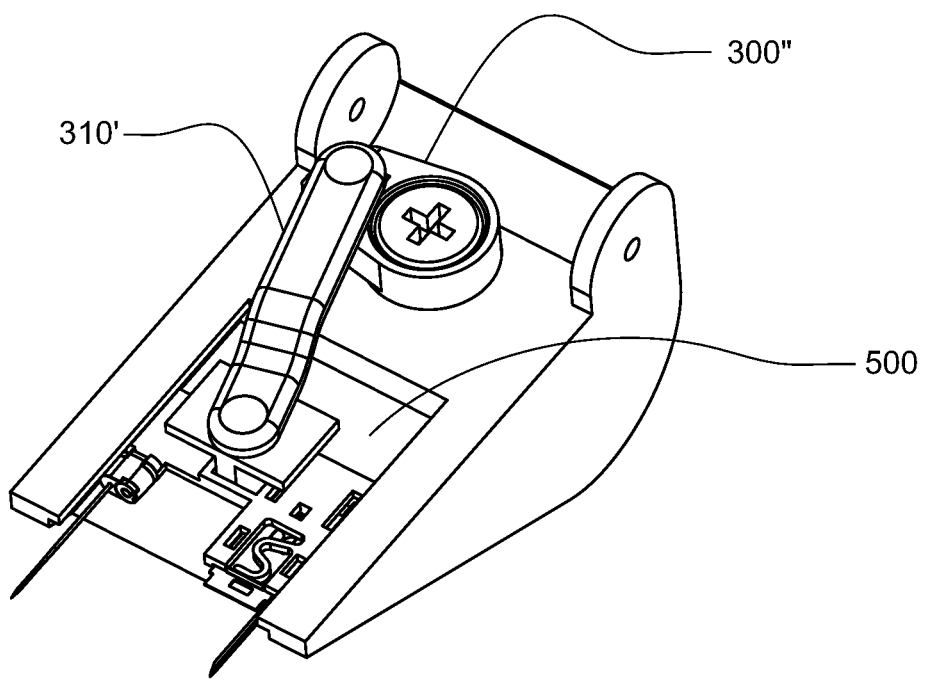
FIG. 9C is a diagrammatic view of an alternative embodiment of the crank assembly of FIG. 9A.

Referring also to FIG. 9C, an alternative crank assembly 300" is shown that utilizes a single linkage assembly (e.g., linkage assembly 310'). Other alternative embodiments may utilize a plurality of crank assemblies (not shown).

As discussed above, first actuator 30 (and/or the second actuator, not shown) may be a spring-based actuator. Referring also to FIG. 10A-10D, an example of such a spring-based actuator is shown. Spring-based actuator 400 may be configured to drive first dermal perforation assembly 12 and/or second dermal perforation assembly 50 (and first insertion needle assembly 28 and/or second insertion needle assembly 54, respectively) downward (as shown in FIGS. 10B-10C) and subsequently upward (as shown in FIGS. 10D-10E).

Figure 11B:
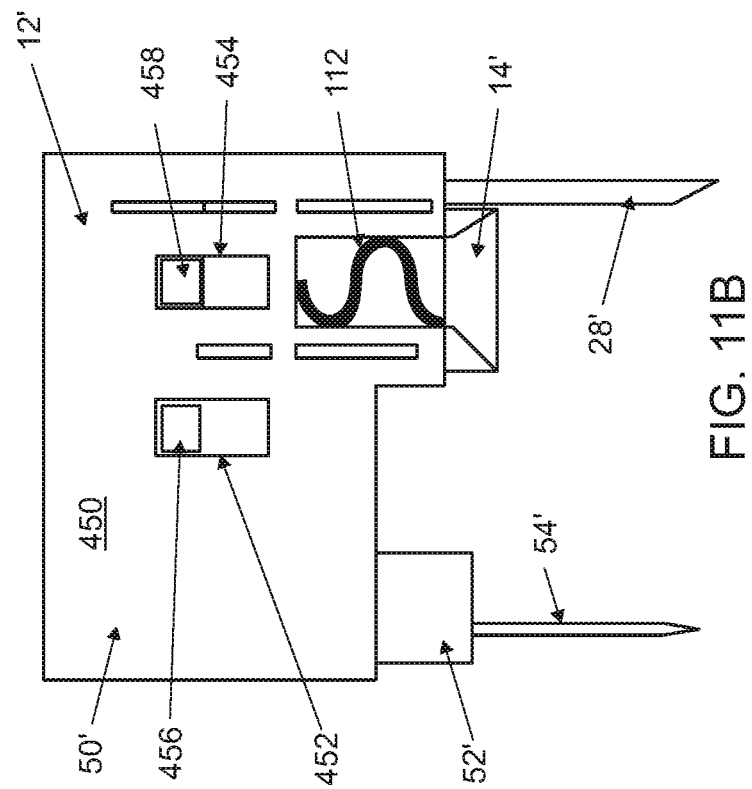
FIGS. 11A-11B are front and back views of a sharps cartridge of automated insertion assembly of FIG. 1.
Figure 11A:
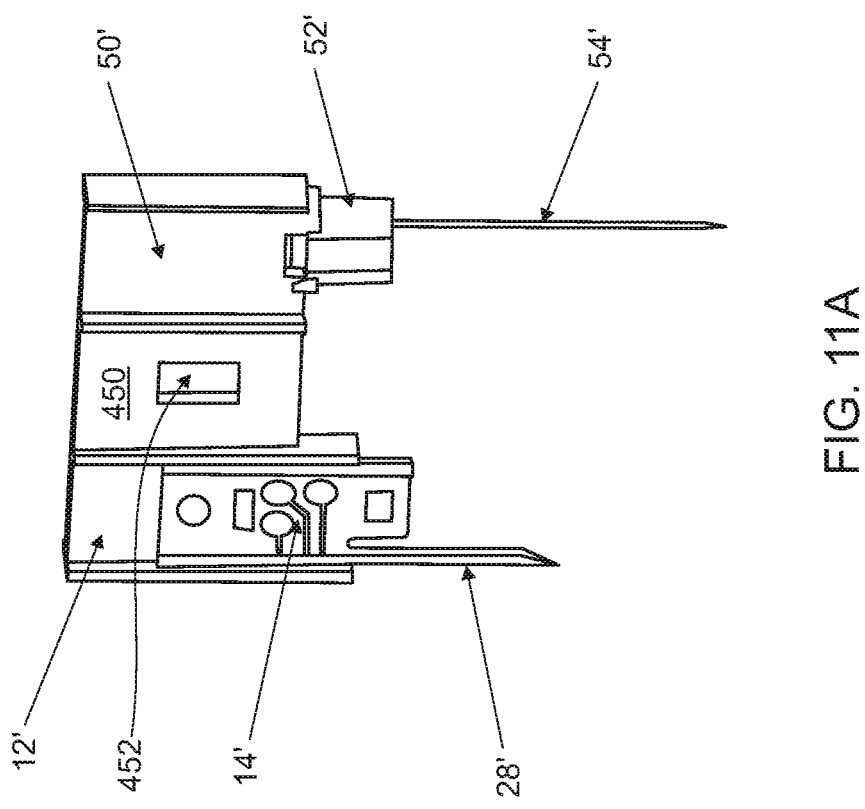

Referring also to FIGS. 11A (front view) and 11B (back view), there is shown first dermal perforation assembly 12' (i.e., an alternative embodiment of first dermal perforation assembly 12) and second dermal perforation assembly 50' (i.e., an alternative embodiment of second dermal perforation assembly 50). Together, the combination of first dermal perforation assembly 12' and second dermal perforation assembly 50' may be referred to as a "sharps cartridge" 450.

As with the above-described system, first dermal perforation assembly 12' may include first insertion needle assembly 28' and second dermal perforation assembly 50' may include second insertion needle assembly 54'. For illustrative purposes and in this particular embodiment, first dermal perforation assembly 12' is shown to be configured to effectuate the insertion of a glucose monitoring probe (i.e., first subdermal device 14') and second dermal perforation assembly 50' is shown to be configured to effectuate the insertion of a cannula assembly (i.e., second subdermal device 52'). Depending on the manner in which the cannula assembly (i.e., second subdermal device 52') is configured, the cannula assembly may or may not include a septum assembly (i.e., a self-sealing and piercable member for establishing fluid communication with a medical device, such as a fluid delivery device).

In this particular embodiment, the cannula assembly (i.e., second subdermal device 52') may be constructed of a semi-rigid/rigid material and therefore may be capable of penetrating user's skin 18 (FIG. 2) without the use of second insertion needle assembly 54' of second dermal perforation assembly 50'. Accordingly and when configured in such a manner, second insertion needle assembly 54' may not be required and, therefore, may not be included within second dermal perforation assembly 50'.

Alternatively, the cannula assembly (i.e., second subdermal device 52') may be constructed of a non-rigid material and, therefore, may be incapable of penetrating user's skin 18 (FIG. 2) without the use of second insertion needle assembly 54'. Accordingly and when configured in such a manner, second insertion needle assembly 54' may be required and, therefore, may be included within second dermal perforation assembly 50'.

Further and in this particular embodiment, the glucose monitoring probe (i.e., first subdermal device 14') may be constructed of a non-rigid material and, therefore, may be incapable of penetrating user's skin 18 (FIG. 2) without the use of first insertion needle assembly 28' and, therefore, may be included within first dermal perforation assembly 12'.

As discussed above, one or more spring assemblies (e.g., spring assemblies 112, 114) may be included within automated insertion assembly 10 to allow for the insertion of one or more of the subdermal devices to a depth (i.e., within user's skin 18) that is deeper than that of the corresponding insertion needle assembly. Accordingly and in this particular embodiment, first dermal perforation assembly 12' is shown to include an alternative embodiment spring assembly (i.e., spring assembly 112'). In this particular example, spring assembly 112' may be a portion of and molded within first dermal perforation assembly 12'. Spring assembly 112' may be sized to provide a mechanical resistance that is sufficient to drive first insertion needle assembly 28' (included within first dermal perforation assembly 12') into user's skin 18.

Once all downward movement of first dermal perforation assembly 12' ceases (due to e.g., encountering a depth stop, as described above), spring assembly 112' may compress and the above-described linkage assembly (e.g., linkage assembly 100) may continue to drive first subdermal device 14' in a downward direction and further into user's skin 18 to a depth (e.g., the above-described second depth) that is deeper than the depth of first insertion needle assembly 28' of first dermal perforation assembly 12' (e.g., the above-described first depth).

In this particular embodiment, sharps cartridge 450 is shown to include slots 452, 454 within which tabs 456, 458 may be positioned. Tabs 456, 458 maybe coupled to the above-described linkage assembly (e.g., linkage assembly 100).

Figure 12:
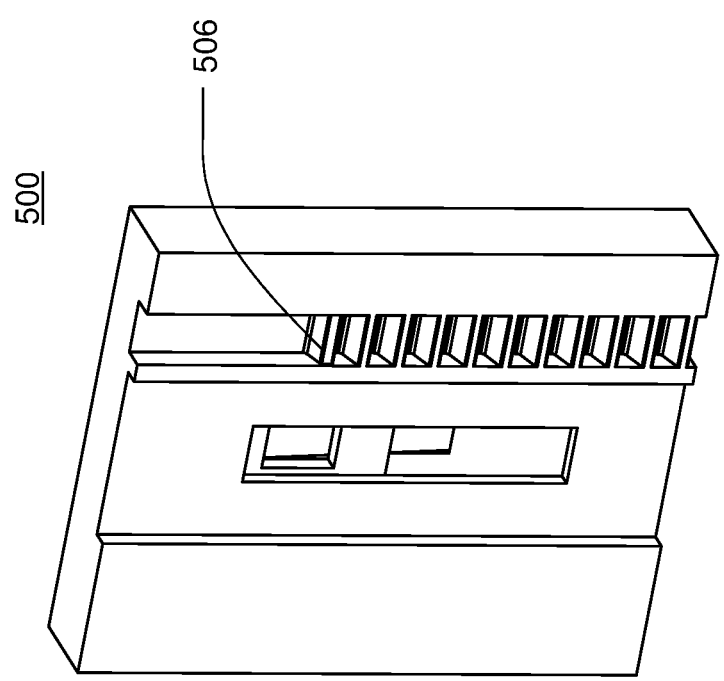
FIG. 12 is an isometric view of a cartridge assembly for housing the sharps cartridge of FIGS. 11A-11B.

Referring also to FIG. 12, there is shown cartridge assembly 500 for carrying sharps cartridge 450, thus protecting the user of sharps cartridge 450 from being accidentally punctured by the glucose monitoring probe (i.e., first subdermal device 14') and/or the cannula assembly (i.e., second subdermal device 52').

Figure 13A:
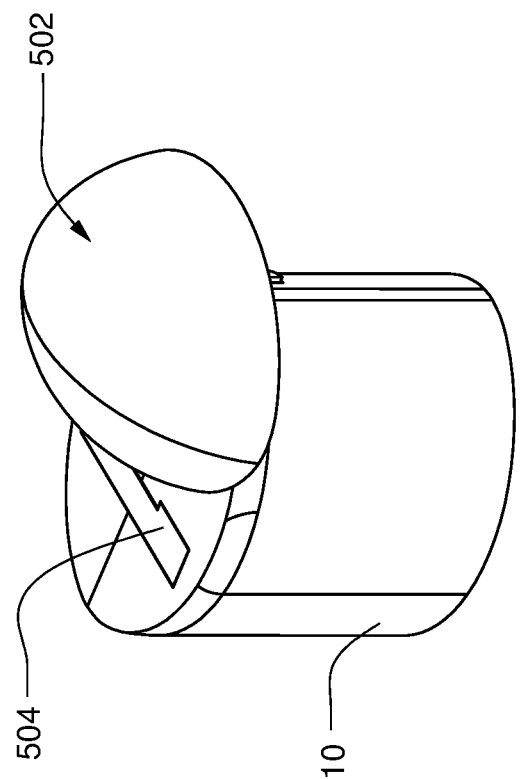
FIGS. 13A-13C are various isometric views of the automated insertion assembly of FIG. 1.
Figure 13C:
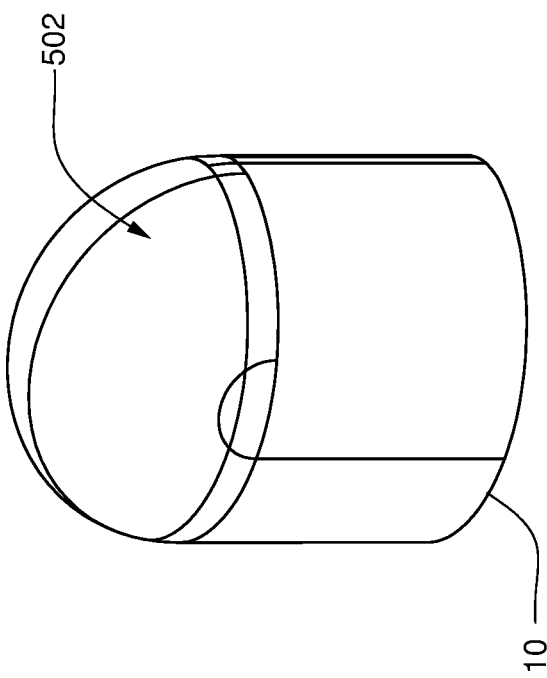
Figure 13B:
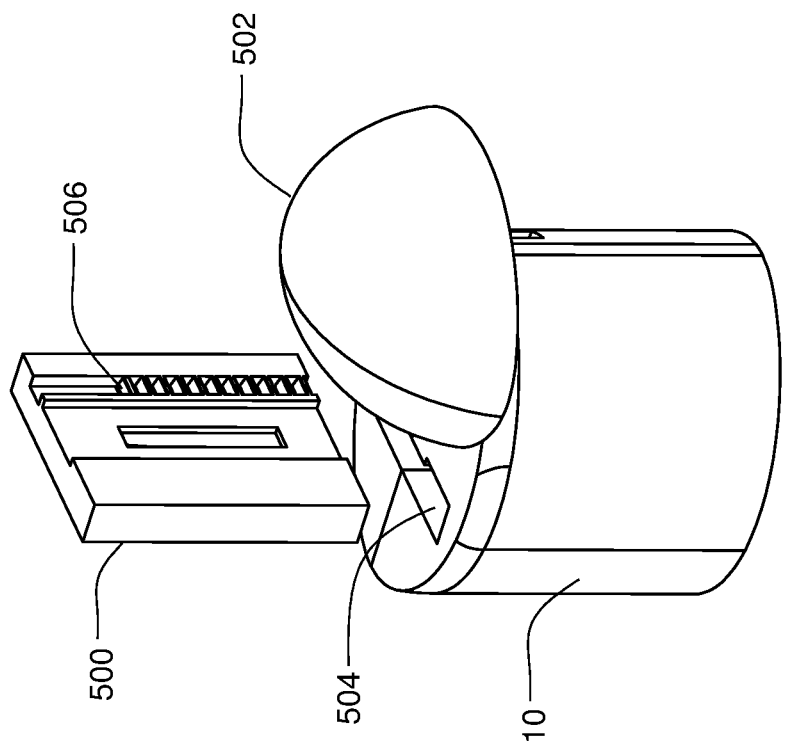

Referring also to FIGS. 13A-13C, there is shown an illustrative and exemplary process for loading cartridge assembly 500 into automated insertion assembly 10. For example and in this embodiment, when loading cartridge assembly 500 into automated insertion assembly 10, the user may pivot cover assembly 502 of automated insertion assembly 10 to expose slot 504 into which cartridge assembly 500 may be placed (as shown in FIG. 13A). Cartridge assembly 500 may include a toothed track 506 for releasably engaging one of the above-described gear assemblies.

Once cover assembly 502 is pivoted, the user may align cartridge 500 with slot 504 in automated insertion assembly 10 (as shown in FIG. 13B) and insert cartridge 500 into automated insertion assembly 10.

Figure 2:
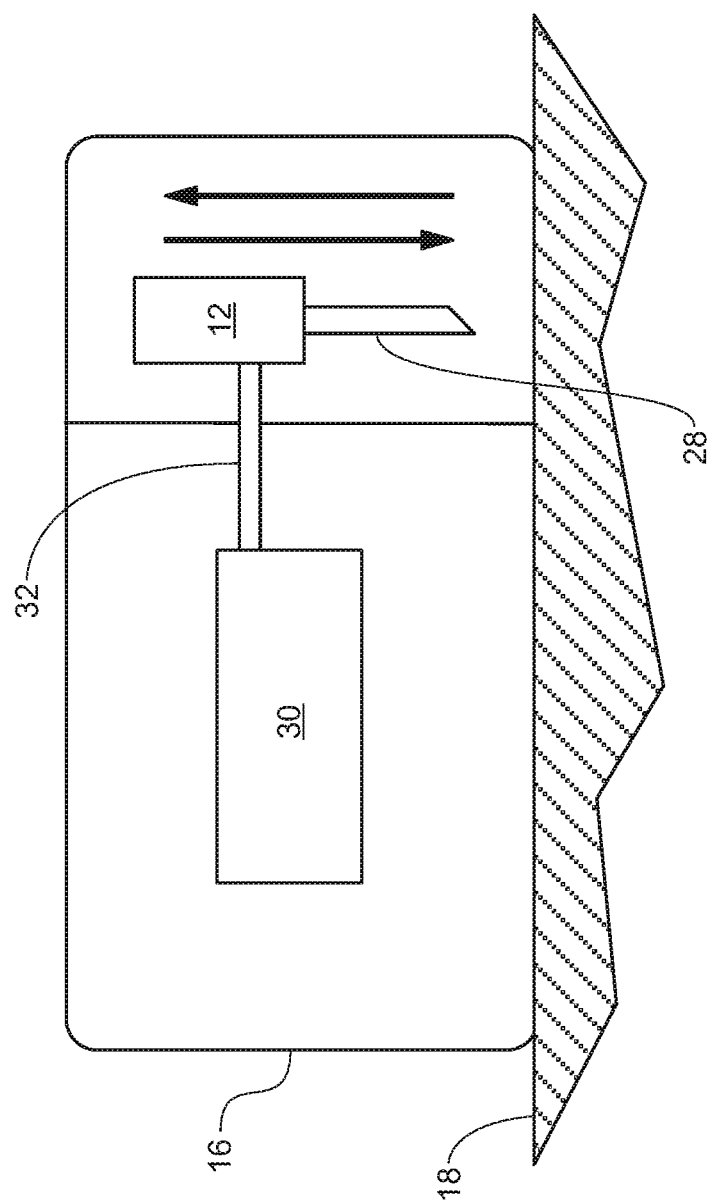
FIG. 2 is another diagrammatic view of the automated insertion assembly of FIG. 1.

In this particular embodiment, insertion of cartridge assembly 500 into slot 504 of automated insertion assembly 10 may result in the "cocking" of the automated insertion assembly 10 to prepare automated insertion assembly 10 to deliver cartridge assembly 500. For example and as discussed above, automated insertion assembly 10 may include first actuation assembly 16 (FIG. 2), which may include first actuator 30 (FIG. 2). As discussed above, examples of first actuator 30 may include but are not limited to a spring-based actuator (not shown), a motor-based actuator (not shown), a pneumatic-based actuator (not shown), and a shape memory wire-based actuator (not shown). Assuming that first actuator 30 is a spring-based actuator, upon the user inserting cartridge assembly 500 into slot 504 of automated insertion assembly 10, first actuator 30 (i.e., a spring-based actuator in this example) may be wound. Alternatively, other "cocking" procedures may be employed, which may include but are not limited to a "cocking" lever (not shown) that winds the above-described spring-based actuator (e.g., first actuator 30).

Once cartridge assembly 500 is fully inserted into slot 504, the user may reverse pivot cover assembly 502 (as shown in FIG. 13C).

As discussed above, when inserting e.g., first subdermal device 14' into user's skin 18, first subdermal device 14' may be inserted to a depth that is greater than the depth to which first insertion needle assembly 28' (included within first dermal perforation assembly 12') is inserted into user's skin 18.

Figure 14A:
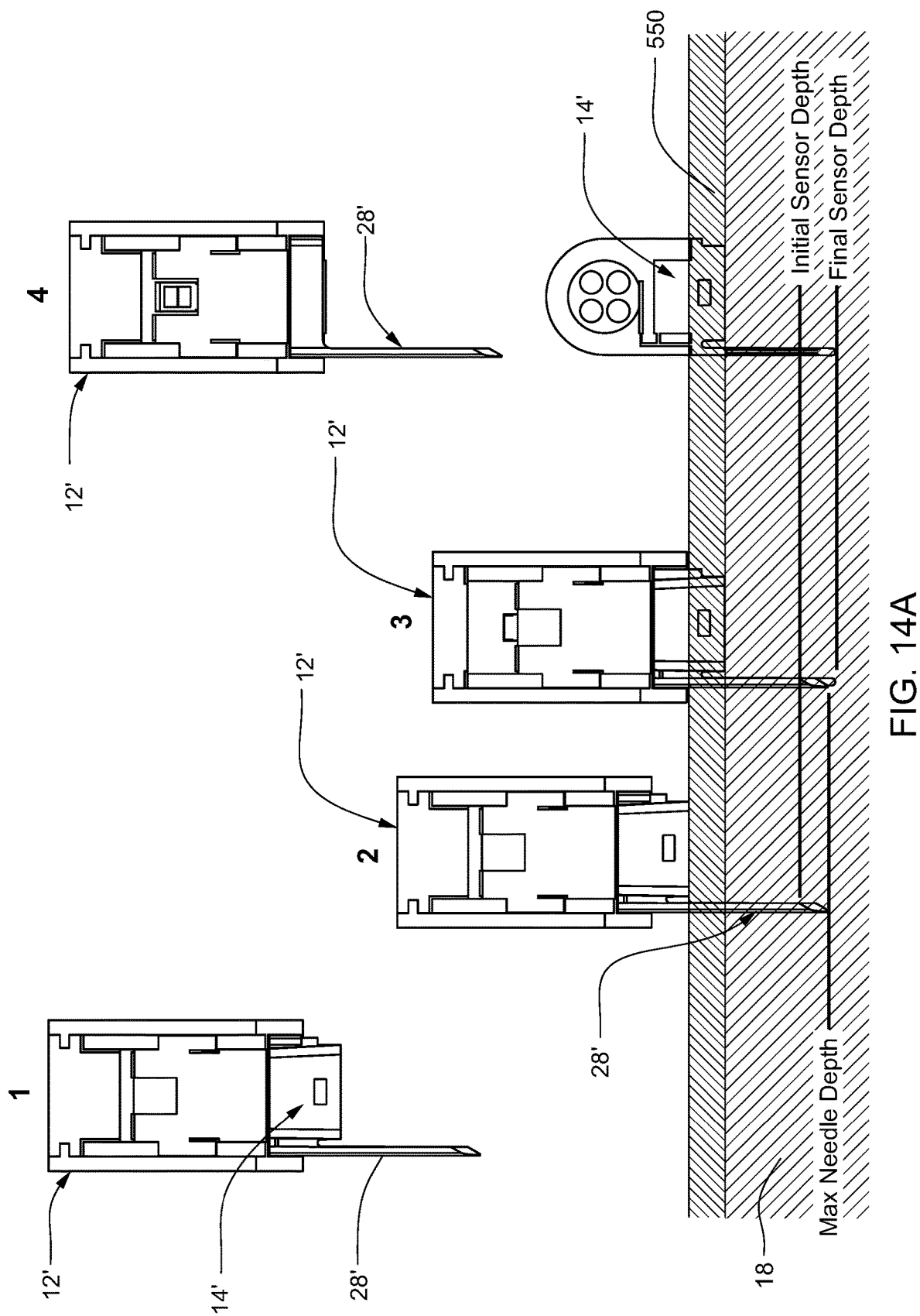
FIG. 14A is a series of views of a dermal perforation assembly of the automated insertion assembly of FIG. 1.
Figure 14B:
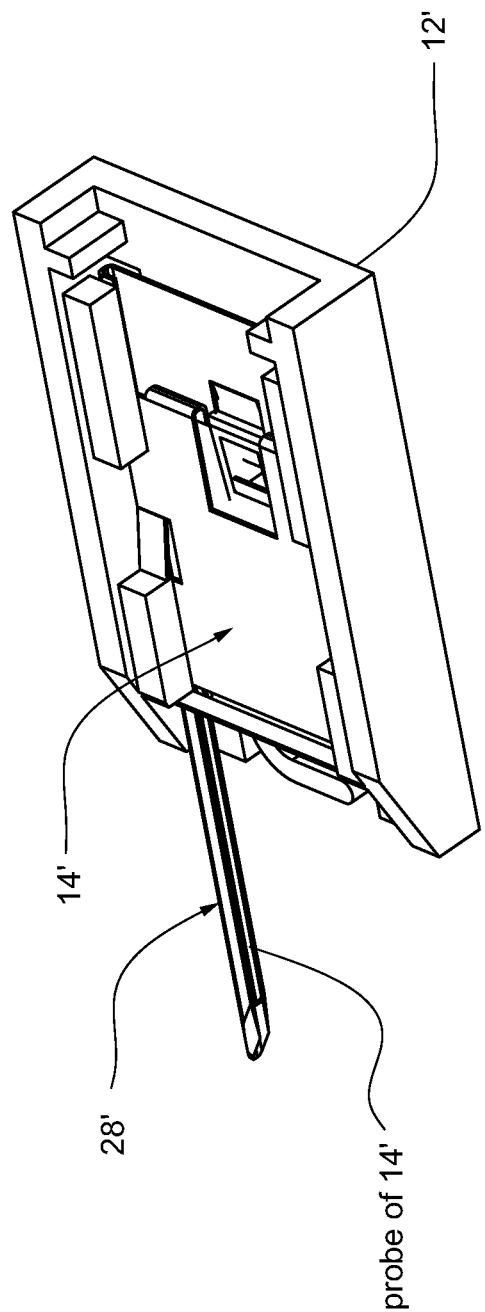
FIG. 14B is an isometric view of the dermal perforation assembly of FIG. 14A.
Figure 15D:
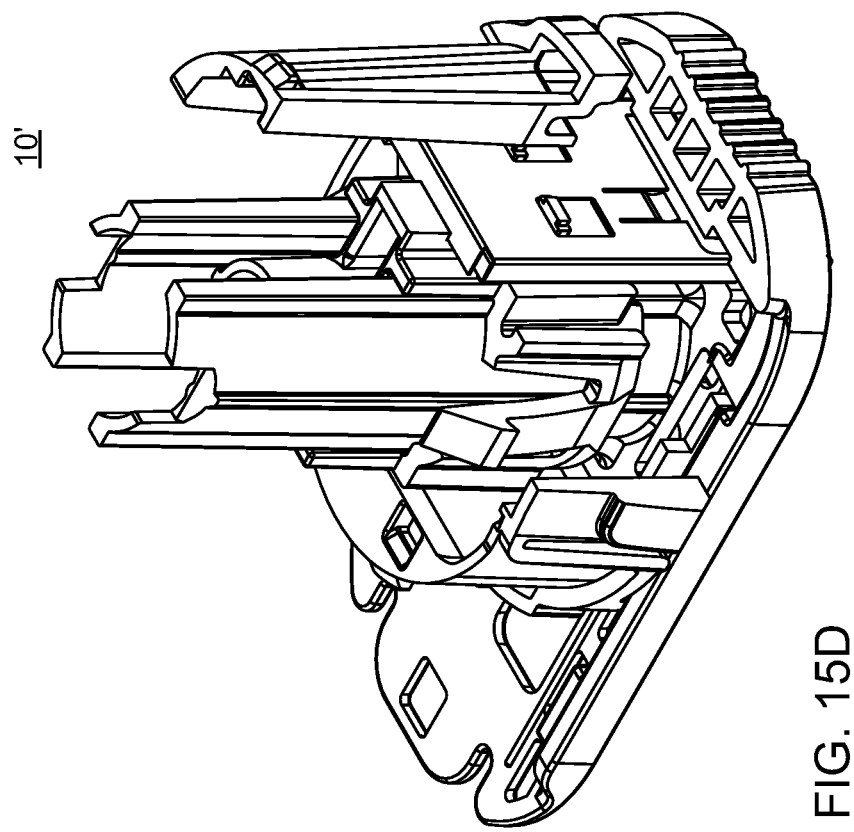
Figure 15C:
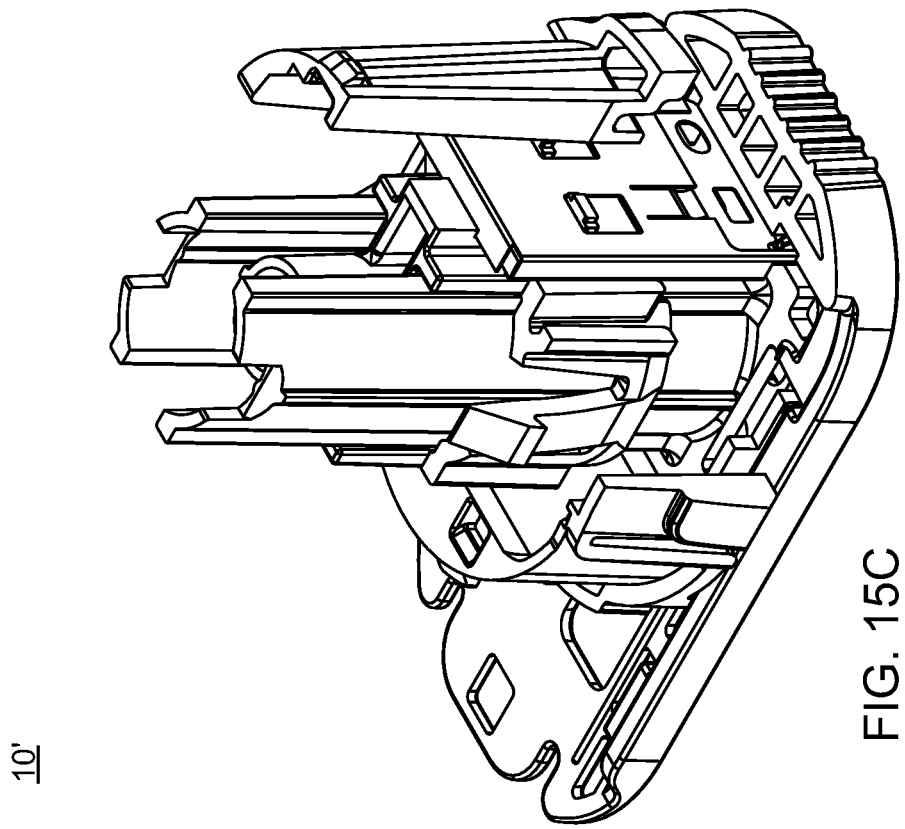
Figure 15F:
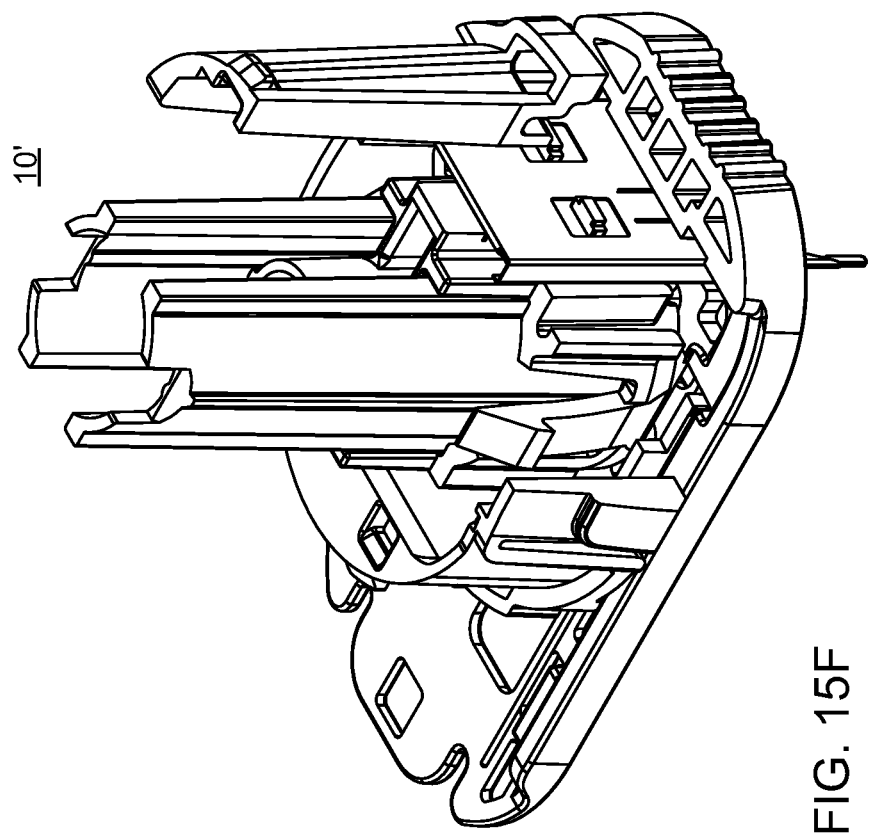
Figure 15E:
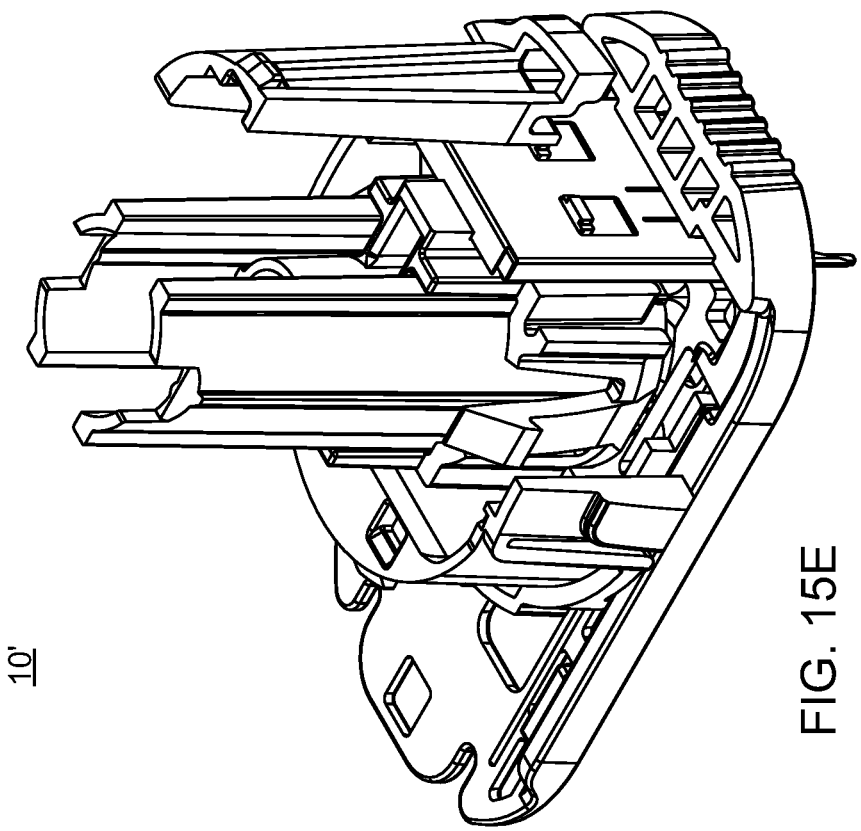
Figure 15H:
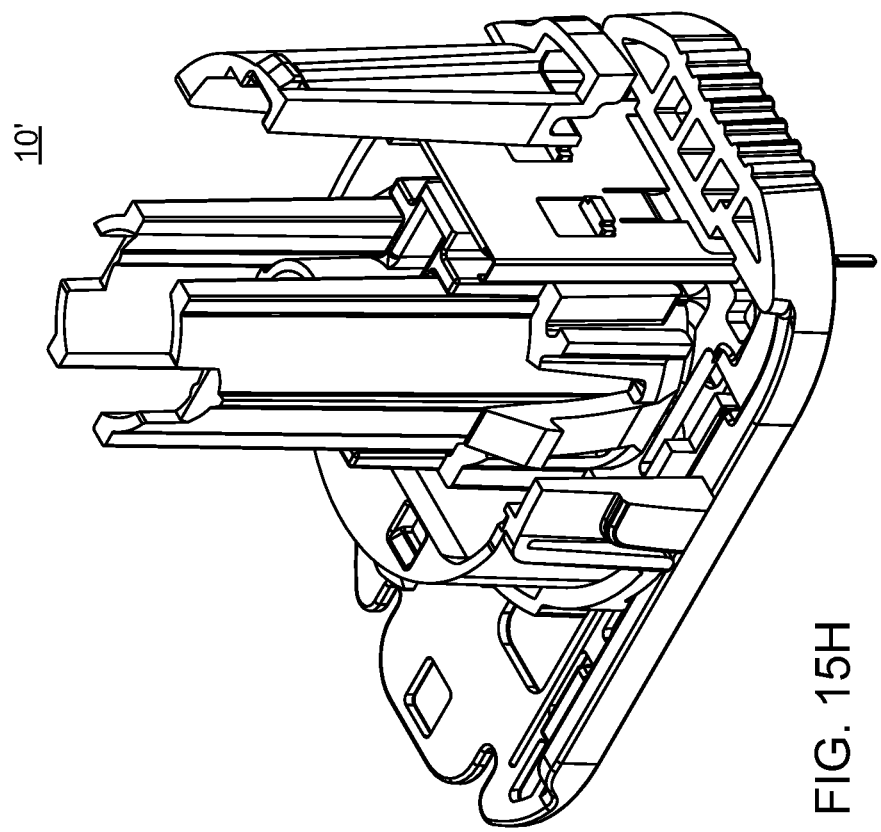
Figure 15G:
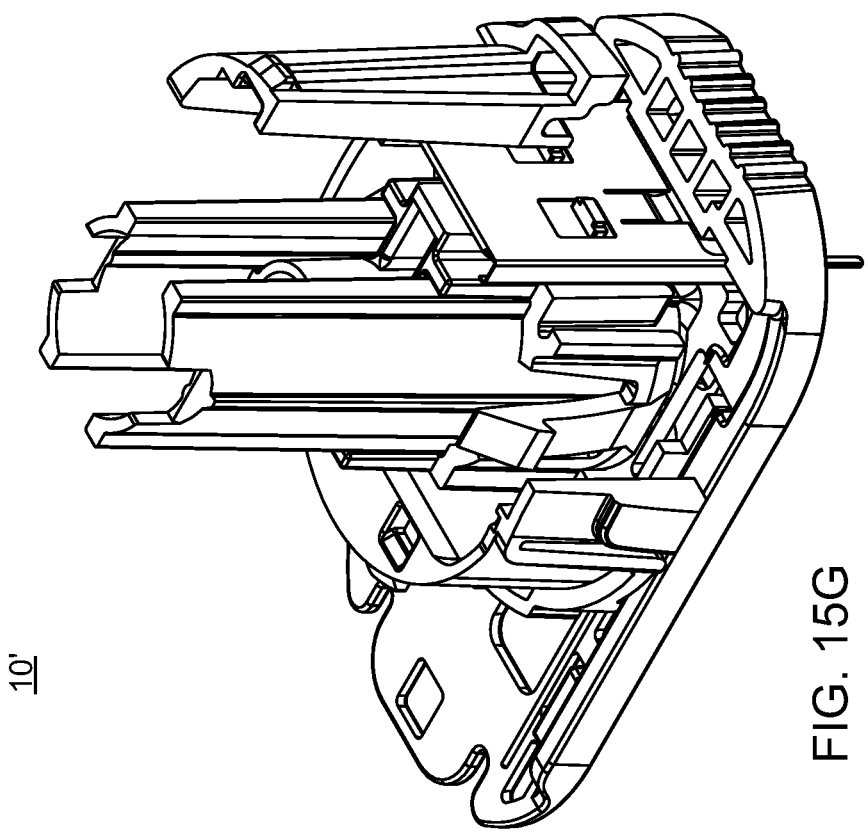
Figure 15J:
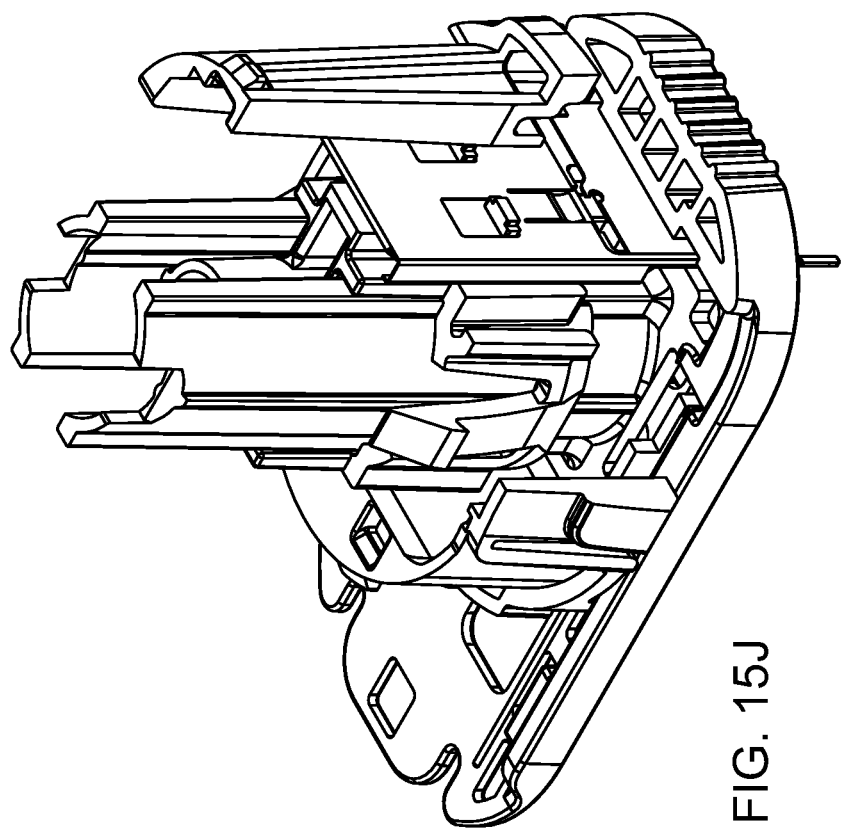
Figure 15I:
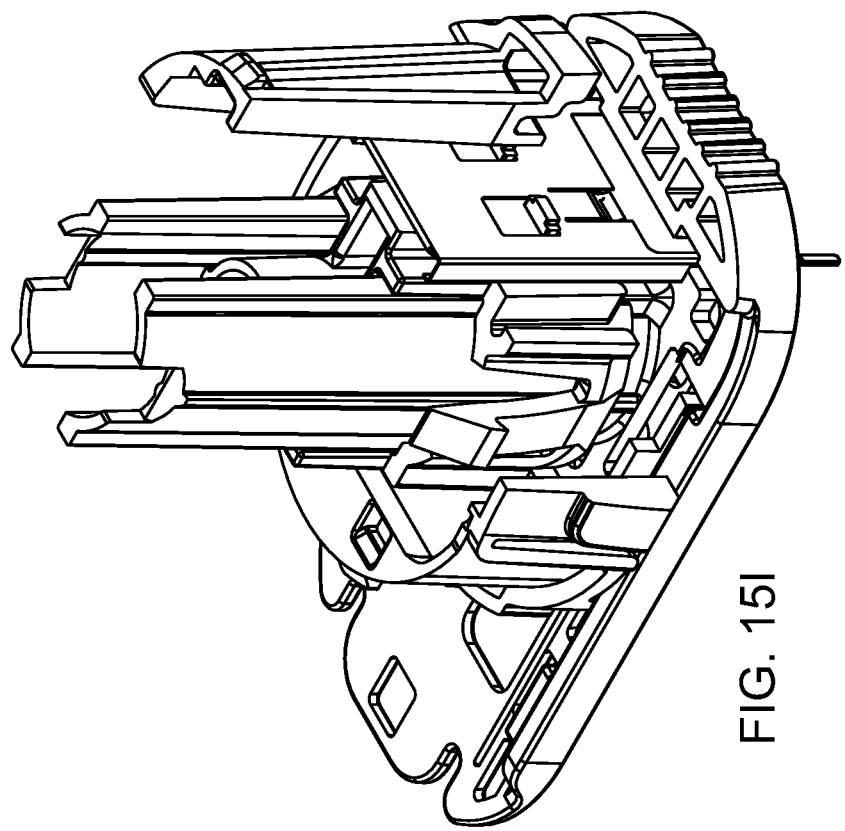
Figure 15L:
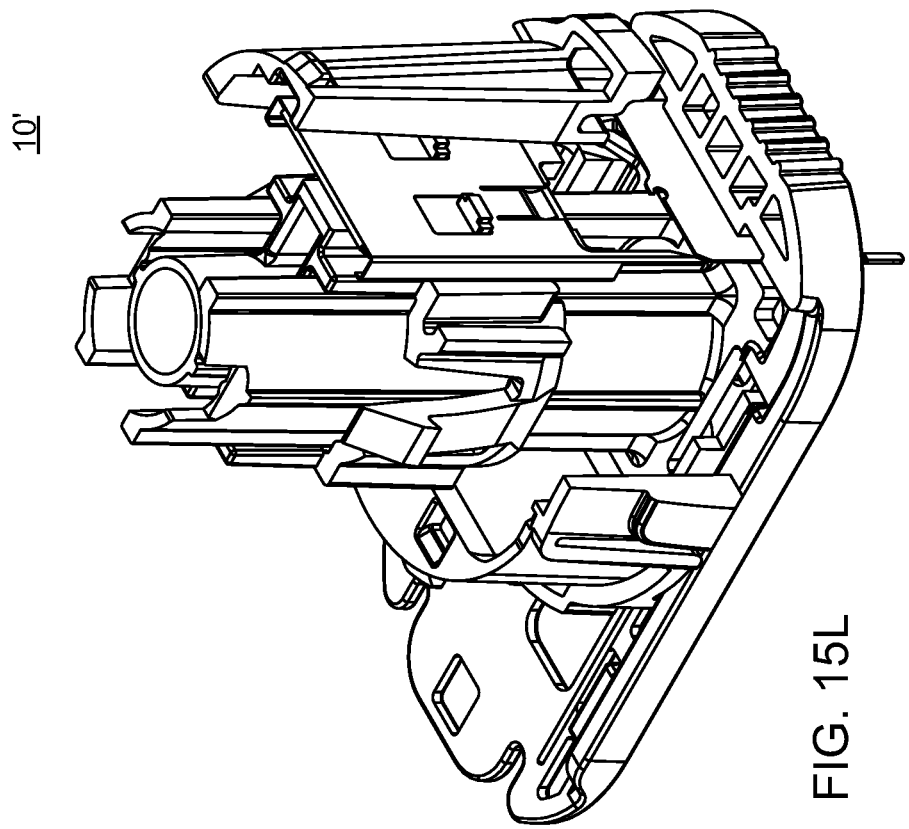
Figure 15K:
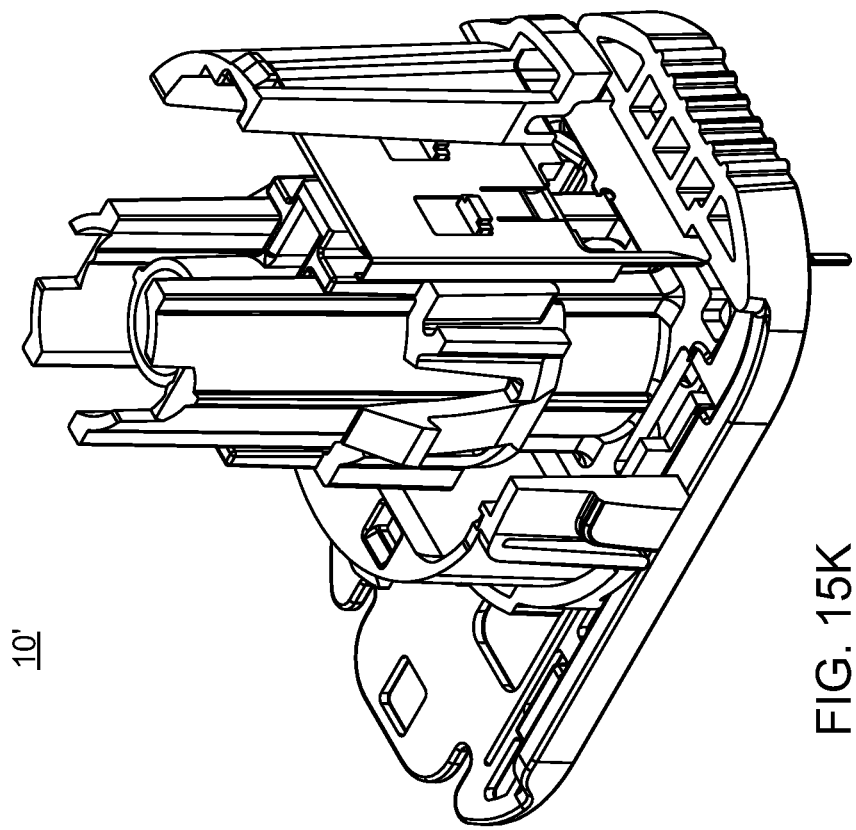

For example and referring also to FIGS. 14A-14B, first dermal perforation assembly 12' may be driven toward user's skin 18. Upon contact with user's skin 18, first insertion needle assembly 28' (included within first dermal perforation assembly 12') may be inserted into user's skin 18. Additionally, first dermal perforation assembly 12' (e.g., a glucose monitoring probe in this example) may also be inserted into user's skin 18. Additional downward force may be applied to first dermal perforation assembly 12' and, for the reasons discussed above, first dermal perforation assembly 12' (e.g., a glucose monitoring probe in this example) may continue to be driven downward (i.e., into user's skin 18).

In this particular embodiment, base 550 of automated insertion assembly 10 may include a recess configured to receive first subdermal device 14', thus allowing first subdermal device 14' to be driven further downward into user's skin 18 to a level that is deeper than that of first insertion needle assembly 28'. Once first subdermal device 14' is positioned at the appropriate depth, first dermal perforation assembly 12' may move upwardly to extract first insertion needle assembly 28' from user's skin 18, resulting in first subdermal device 14' disconnecting from first dermal perforation assembly 12', thus allowing first dermal perforation assembly 12' to remain within user's skin 18.

Referring also to FIG. 15A-15L, there is shown a series of illustrations of another embodiment of automated insertion assembly 10 (i.e., automated insertion assembly 10'). In this particular embodiment, automated insertion assembly 10' may includes actuator platform 600 that is slidably seated upon one or more carriage guides (e.g., carriage guide 602) that may be driven by e.g., first actuator 30 included within actuation assembly 16. As discussed above, examples of first actuator 30 may include but are not limited to a spring-based actuator (not shown), a motor-based actuator (not shown), a pneumatic-based actuator (not shown), and a shape memory wire-based actuator (not shown).

First dermal perforation assembly 12', second dermal perforation assembly 50' and/or cartridge assembly 500 (which was described above as including first dermal perforation assembly 12', and second dermal perforation assembly 50') may be releasably attached to (e.g., clipped to) actuator platform 600 via one or more clip regions/assemblies (not shown). One or more tabs (e.g., tabs 456, 458) may protrude through slots 452, 454 (FIG. 11) within e.g., first dermal perforation assembly 12', second dermal perforation assembly 50' and/or cartridge assembly 500. As actuator platform 600 travels toward user's skin 18 (FIG. 2), the various insertion needle assemblies may penetrate user's skin 18. When (for the reasons discussed above), first dermal perforation assembly 12', second dermal perforation assembly 50' and/or cartridge assembly 500 can no longer travel in a downward direction (i.e., toward user's skin 18), first subdermal device 14' and/or second subdermal device 52' may continue to be driven downward (i.e., into user's skin 18) until the desired depth is achieved (which e.g., may be greater than the depth of first insertion needle assembly 28' and/or second insertion needle assembly 54'). Once properly inserted, actuator platform 600 may begin traveling upward, extracting first dermal perforation assembly 12', second dermal perforation assembly 50' and/or cartridge assembly 500.

As discussed above, automated insertion assembly 10 may include one or more gear assemblies that may be configured to at least partially couple the actuators (e.g., first actuator 30) included within automated insertion assembly 10 to the dermal perforation assemblies (e.g., first dermal perforation assembly 12) included within automated insertion assembly 10.

Figure 16:
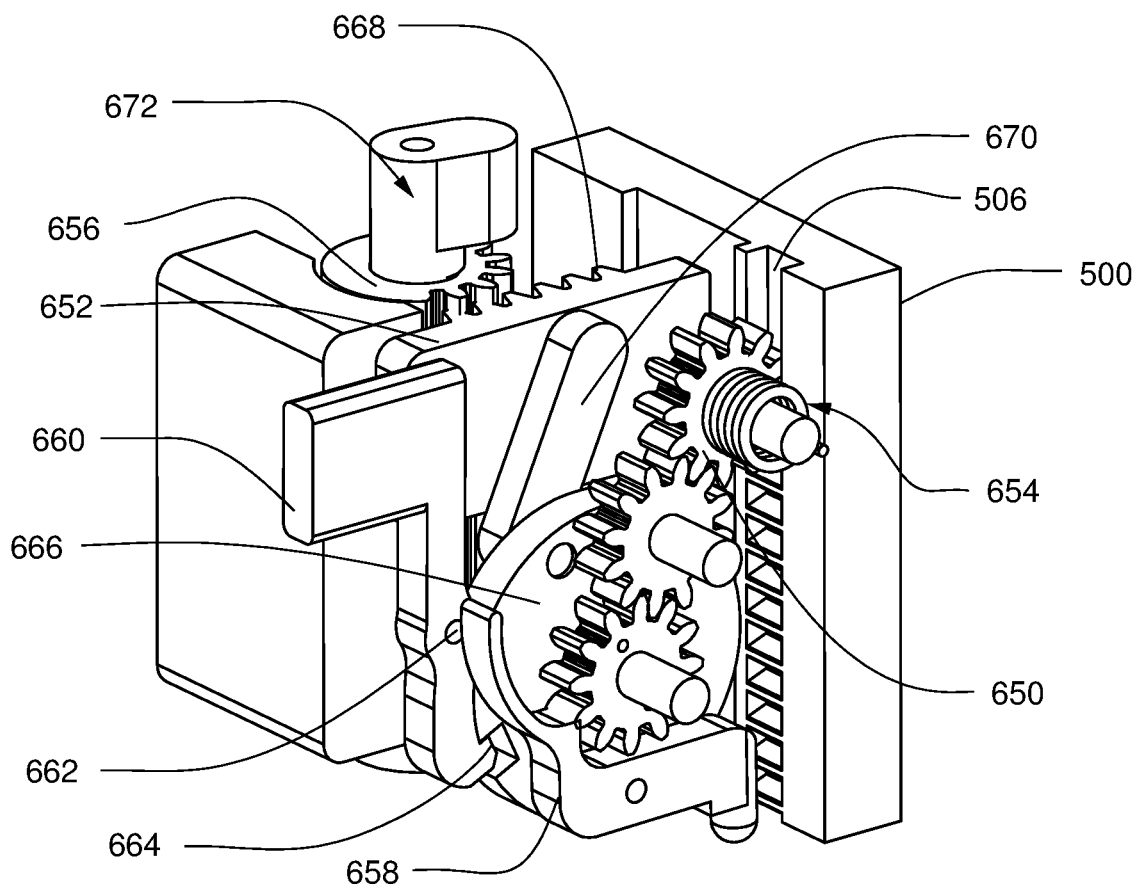
FIGS. 16-18 are isometric views of a gear assembly/actuator of the automated insertion assembly of FIG. 1.
Figure 17:
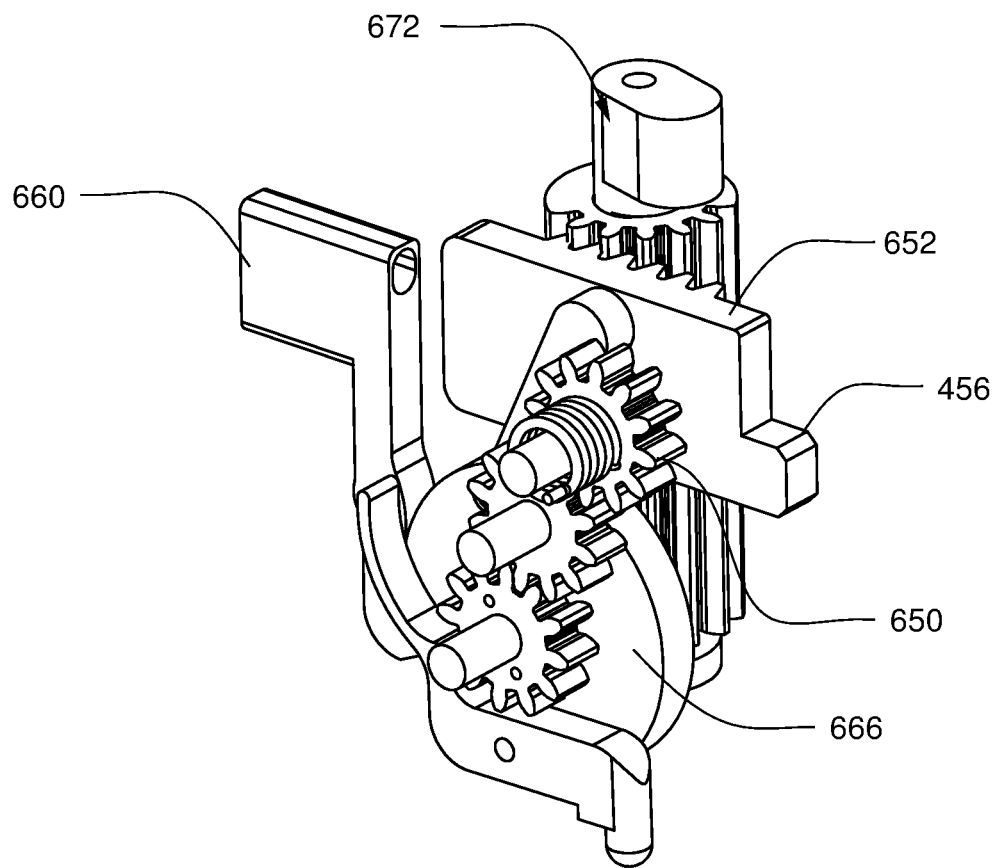

Referring also to FIGS. 16-17, there is shown one embodiment of the above-described gear assemblies coupled to one embodiment of an actuator (e.g., first actuator 30). In this particular embodiment, automated insertion assembly 10 is shown in the above-described "cocked" position, as cartridge assembly 500 is shown in a position that is indicative of being inserted within automated insertion assembly 10. As discussed above, when in the "cocked" position, the various insertion needle assemblies included within cartridge assembly 500 are ready to be inserted into user's skin 18. When inserting cartridge assembly 500 into automated insertion assembly 10, toothed track 506 within cartridge assembly 500 may releasably engage the uppermost gear of drive gear set 650, resulting in the uppermost gear rotating clockwise, raising actuator 652, and winding torsion spring 654 (i.e., the actuator), thus "cocking" automated insertion assembly 10 with sufficient potential energy to insert the various insertion needle assemblies and subdermal devices into user's skin 18.

Once "cocked", torsion spring 654 may also have enough stored energy to remove the various insertion needle assemblies, while leaving the subdermal devices within user's skin 18. After full insertion of cartridge assembly 500 into automated insertion assembly 10, the uppermost gear within drive gear set 650 may be seated in a toothless groove and, therefore, may spin freely upon actuation without moving cartridge assembly 500.

Prior to closing cover assembly 502 (FIGS. 13A-13C), actuator 652 may be placed into a retracted position by rotating retraction gears 656. The process of retracting actuator 652 may be accomplished via e.g., cover assembly 502. Accordingly, when closing cover assembly 502, retraction gears 656 may rotate in the opposite direction, inserting e.g., tabs 456, 458 (FIGS. 11A-11B) into slots 452, 454 (FIGS. 11A-11B). Safety catch 658 may be used to prevent the untimely "firing" of cartridge assembly 500 into user's skin 18.

To activate this particular embodiment of automated insertion assembly 10, the upper portion of release lever 660 may be pushed forward, causing release lever 660 to pivot about fulcrum 662 and disengage trigger catch 664 from a cooperatively shaped recess in drive wheel 666. Torsion spring 654 may then cause drive gear set 650 to rotate, turning drive wheel 666 and lowering actuator 652. As actuator 652 is lowered, teeth 668 within actuator 652 will slide through the longitudinal grooves in retraction gear 656. The use of drive wheel 666 and the connecting rod assemblies (e.g., connecting rod 670) may result in a sinusoidal insertion velocity (with respect to the various insertion needle assemblies included within sharps cartridge 500). Other insertion velocity profiles may be created by e.g., replacing drive wheel 666 with a cam assembly (not shown).

Figure 18:
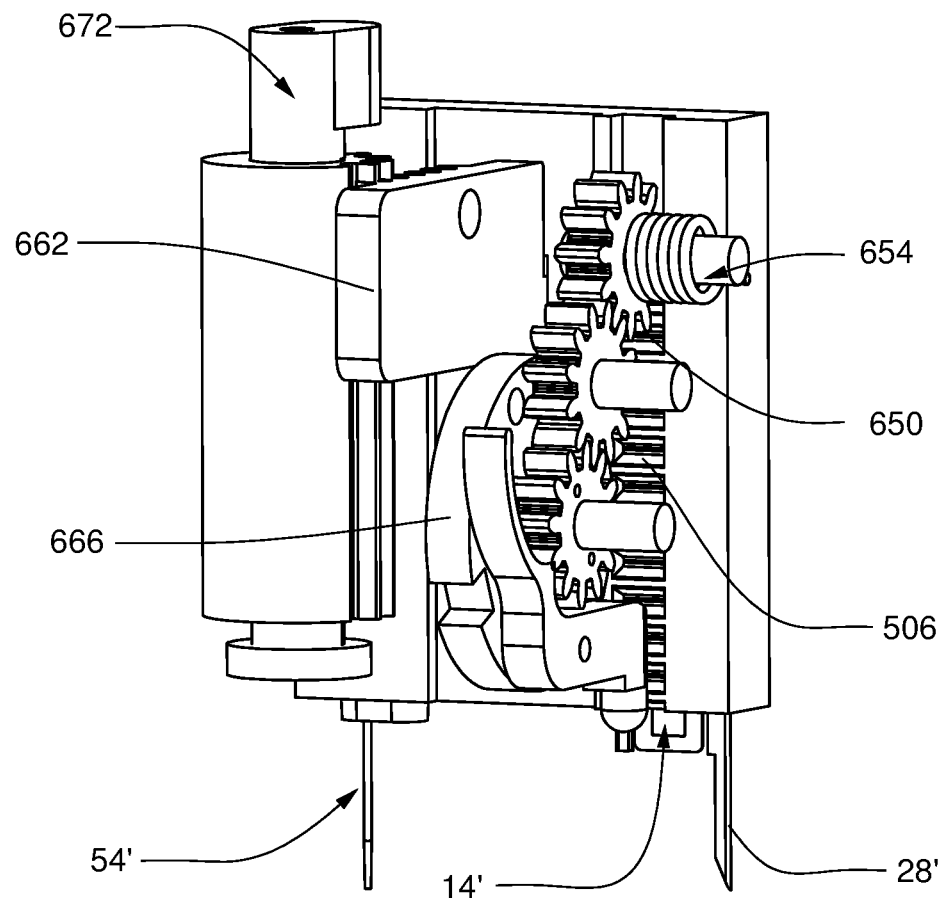

Referring also to FIG. 18, there is shown the above-described gear assembly/actuator (i.e., of FIGS. 16-17) after "firing", that is after insertion of insertion needle assemblies 28'. 54' into user's skin 18. Typically, drive wheel 666 is configured so that after insertion of insertion needle assemblies 28' 54' (and the associated subdermal devices), drive wheel 666 has sufficient momentum to continue to rotate, thus extracting insertion needle assemblies 28' 54' from user's skin 18. Depending upon the design of drive wheel 666 and the connecting rod(s), the kinetic profile of insertion and withdrawal may approximate a sine-wave, i.e., starting slowly, accelerating and then slowing down again.

If retraction gear shaft 672 is coupled to cover assembly 502, the opening of cover assembly 502 may actuate the retraction by disengaging tabs 456, 458 (FIGS. 11A-11B) from slots 452, 454 (FIGS. 11A-11B), thus allowing removal of cartridge assembly 500 from automated insertion assembly 10. Automated insertion assembly 10 may then be ready for reuse with a replacement sharps cartridge. One or more spring assemblies may cause cartridge assembly 500 to pop up out of slot 504 to simplify removal.

In one embodiment of automated insertion assembly 10, drive wheel 666 may not rotate a full 360°, but a lesser amount, e.g., 330°. In this particular embodiment, actuator 652 may "top-out" prior to the complete 360° rotation of drive wheel 666, thus resulting in e.g., cartridge assembly 500 being partially pushed out of slot 504 (thus facilitating easy removal from automated insertion assembly 10).

A number of implementations have been described. Nevertheless, it will be understood that various modifications may be made. Accordingly, other implementations are within the scope of the following claims.

What is claimed is:

1. An automated insertion system comprising:
   a cartridge assembly comprising:
      a toothed track;
      a toothless track; and
      at least one dermal perforation assembly having an interior passage configured to releasably engage at least a portion of a subdermal device therein; and
   an actuation assembly configured to drive the at least one dermal perforation assembly a predetermined distance, the actuation assembly comprising:
   a drive gear set for engaging the cartridge assembly;
   an actuator; and
   a spring,
   wherein when a gear of the drive gear set is engaged with the toothed track of the cartridge assembly, the actuator is raised and potential energy is stored in the spring,
   wherein the spring is configured to convert the potential energy to drive the at least one dermal perforation assembly the predetermined distance, the gear of the drive gear set is seated in the toothless groove track after the at least one dermal perforation assembly is driven the predetermined distance.

2. The automated insertion system of claim 1 wherein the subdermal device is chosen from the group consisting of a cannula assembly and a probe.

3. The automated insertion system of claim 1 wherein the at least one dermal perforation assembly comprising:
   a first insertion needle assembly for at least partially encapsulating at least a portion of the subdermal device.

4. The automated insertion system of claim 1 wherein the actuation assembly comprising:
   an actuator for providing mechanical energy sufficient to drive the at least one dermal perforation assembly the predetermined distance.

5. The automated insertion system of claim 4 wherein the actuator is a spring-based actuator.

6. The automated insertion system of claim 4 wherein the actuation assembly comprising:
   one or more gear assemblies for at least partially coupling the actuator to the at least one dermal perforation assembly.

7. The automated insertion system of claim 4 wherein the actuation assembly comprising:
   one or more linkage assemblies for at least partially coupling the actuator to the at least one dermal perforation assembly.

8. The automated insertion system of claim 1 further comprising:
   at least two dermal perforation assemblies comprising a first dermal perforation assembly and a second dermal perforation assembly, the at first and second dermal perforation assemblies configured to releasably engage a first subdermal device and a second subdermal device respectively; and
   a second actuation assembly configured to drive the second dermal perforation assembly.

9. The automated insertion system of claim 8 wherein the second subdermal device is chosen from the group consisting of a cannular assembly and a probe.

10. The automated insertion system of claim 8 wherein the second dermal perforation assembly comprising:
    a second insertion needle assembly for at least partially encapsulating at least a portion of the second subdermal device.

11. The automated insertion system of claim 8 wherein the second actuation assembly comprising:
    a second actuator for providing mechanical energy sufficient to drive the second dermal perforation assembly a predetermined distance.

12. The automated insertion system of claim 11 wherein the second actuator is a spring-based actuator.

13. The automated insertion system of claim 11 wherein the second actuation assembly comprising:
    one or more gear assemblies for at least partially coupling the second actuator to the second dermal perforation assembly.

14. The automated insertion system of claim 11 wherein the second actuation assembly comprising:
    one or more linkage assemblies for at least partially coupling the second actuator to the second dermal perforation assembly.

* * * * *